United States Patent [19]
Mizoguchi et al.

[11] Patent Number: 5,781,878
[45] Date of Patent: Jul. 14, 1998

[54] APPARATUS AND METHOD FOR DIAGNOSING DEGRADATION OR MALFUNCTION OF OXYGEN SENSOR

[75] Inventors: Tomomichi Mizoguchi, Aichi-ken; Masayuki Takami, Kariya; Kazuhiro Okazaki, Anjo, all of Japan

[73] Assignee: Nippondenso Co., Ltd., Kariya, Japan

[21] Appl. No.: 655,097

[22] Filed: Jun. 4, 1996

[30] Foreign Application Priority Data

Jun. 5, 1995 [JP] Japan .................................. 7-138244
Jun. 13, 1995 [JP] Japan .................................. 7-146549

[51] Int. Cl.⁶ .................................................. G01M 15/00
[52] U.S. Cl. ........................ 701/109; 73/23.32; 73/118.1
[58] Field of Search ............................ 701/109, 103; 73/23.31, 23.32, 118.1, 117.3; 340/438, 439

[56] References Cited

U.S. PATENT DOCUMENTS

| | | | |
|---|---|---|---|
| 4,419,190 | 12/1983 | Dietz et al. | 204/1 T |
| 4,543,176 | 9/1985 | Harada et al. | 204/406 |
| 5,405,521 | 4/1995 | Nakamori et al. | 204/425 |
| 5,547,552 | 8/1996 | Hasegawa et al. | 204/425 |

FOREIGN PATENT DOCUMENTS

| | | |
|---|---|---|
| 60-192849 | 10/1985 | Japan . |
| 62-198751 | 9/1987 | Japan . |
| 1-262460 | 10/1989 | Japan . |
| 3-21859 | 1/1991 | Japan . |
| 4-24657 | 4/1992 | Japan . |
| 4-233447 | 8/1992 | Japan . |
| 7-18837 | 3/1995 | Japan . |

*Primary Examiner*—George M. Dombroske
*Attorney, Agent, or Firm*—Cushman Darby & Cushman IP Group of Pillsbury Madison & Sutro LLP

[57] ABSTRACT

An oxygen sensor has a detecting device unit for outputting a sensor current such as a limiting current of which a value is constant even though a sensing voltage applied to the oxygen sensor changes in a limiting current generating region and corresponds to an air-fuel ratio of a combustion gas and a heater for heating the detecting device unit to keep a resistance of the detecting device unit even though the oxygen sensor is degraded. When the sensing voltage is changed to a second sensing voltage of a resistance governing region, a current peak occurs in the sensor current, and a peak current value is detected. Because the peak current value decreases as the oxygen sensor is gradually degraded, when the peak current value is lower than a degradation judging value, it is judged that the oxygen sensor is degraded. Therefore, the diagnosis of the degradation of the oxygen sensor can be performed with a high accuracy.

16 Claims, 18 Drawing Sheets

APPARATUS AND METHOD FOR DIAGNOSING DEGRADATION OR MALFUNCTION OF OXYGEN SENSOR

BACKGROUND OF THE INVENTION

1. Field of the Invention

The present invention relates to degradation diagnosing apparatus and method applied for a limiting current type oxygen sensor. Also, the present invention relates to a malfunction diagnosing method applied for a limiting current type oxygen sensor.

2. Description of the Related Art

A limiting current type oxygen sensor has been recently adopted to linearly detect an air-fuel ratio in a combustion gas, for example, burned in an automobile engine according to an oxygen concentration of an exhaust gas. In this limiting current type oxygen sensor, a limiting current having a constant value is output in a certain range of a voltage supplied to the oxygen sensor, and the constant value of the limiting current changes in proportion to an oxygen concentration. Therefore, in cases where the limiting current type oxygen sensor is used for an air-fuel ratio control system of the automobile engine, an air-fuel ratio in a combustion gas can be determined according to a value of the limiting current output from the limiting current type oxygen sensor.

2.1. Previously Proposed Art

Also, a technique for accurately detecting a degree of degradation of the oxygen sensor changing with the passage of time is expected. As this technique, a method for detecting deterioration in exhaust density sensor is, for example, disclosed in a Published Unexamined Japanese Patent Application No. 4-233447 of 1992. In this application, an internal resistance of an oxygen sensor is calculated from an output current (or a limiting current) of the oxygen sensor obtained when a voltage is supplied to the oxygen sensor, and it is diagnosed that the oxygen sensor is degraded when a value of the internal resistance is increased.

Also, a technique for accurately detecting malfunction of the oxygen sensor is expected. As this technique, a diagnosing method for self-diagnosing deterioration of an oxygen sensor is, for example, disclosed in a Published Unexamined Japanese Patent Application No. 1-262460 of 1991. In this application, an applied voltage gradually changes in a flatness region (or a limiting current generating region) defined in a voltage-current characteristic of the oxygen sensor, and a degree of degradation of the oxygen sensor is diagnosed according to a reduction degree of a limiting current.

2.2. Problems to be Solved by the Invention

However, it is required in the Application No. 4-233447 to keep a temperature of a solid electrolyte layer of the oxygen sensor at a prescribed active temperature (for example, 650° C.) for the purpose of detecting the limiting current with a high accuracy. Therefore, a heater is arranged in the oxygen sensor, and an electric current supplied to the heater is controlled to keep the temperature of the solid electrolyte layer of the oxygen sensor. In this case, even though the oxygen sensor is degraded to increase the internal resistance, because a value of the electric current supplied to the heater is increased to compensate for the increase of the internal resistance, the internal resistance is kept at a constant value. Therefore, there is a drawback that a degradation diagnosis for the oxygen sensor cannot be performed even though the oxygen sensor is actually degraded.

Also, in the Application No. 1-262460, malfunction of the oxygen sensor cannot be detected when malfunction of the oxygen sensor occurs and a sensor output does not change because of a disconnection or the like. That is, in the diagnosing method of the application, in cases where the sensor output is maintained to 0 mA because of the occurrence of a disconnection malfunction, there is a probability that the oxygen sensor is erroneously judged to be set in a normal condition. Also, in cases where the oxygen sensor is judged to be set in a disconnection malfunction condition when the sensor output (or the limiting current) is maintained to 0 mA, because the sensor output (or the limiting current) is maintained to 0 mA at an ideal air-fuel ratio while the oxygen sensor is normally operated, a malfunction judgement cannot be reliably performed when the sensor output is merely judged.

An example is described with reference to FIGS. 22A and 22B. FIGS. 22A and 22B respectively show a malfunction condition of an oxygen sensor. When a device crack of the oxygen sensor occurs or a wire harness is disconnected, a malfunction of the oxygen sensor occurs. In this case, as shown in FIG. 22A, a characteristic line L6 indicating a voltage-current characteristic of the oxygen sensor agrees with a line of a sensor current Is=0. Also, when a connector electrically connected with an oxygen sensor is about to be disconnected or rust occurs in a conducting line of the connector, a conducting resistance of the connector increases from 100 to 200 k$\Omega$ though the conducting resistance is normally 1 $\Omega$, and a conducting defect occurs in the connector. In this case, as shown in FIG. 22B, a characteristic line L7 indicating a voltage-current characteristic of the oxygen sensor almost agrees with a line of a sensor current Is =0. That is, a sensor current slightly flows because of the malfunction of the connector.

SUMMARY OF THE INVENTION

A first object of the present invention is to provide, with due consideration to the drawback of such a conventional degradation diagnosing method, apparatus and method for diagnosing degradation of an oxygen sensor in which a degradation diagnosis for an oxygen sensor is performed with a high accuracy even though a value of an electric current supplied to a heater of the oxygen sensor is controlled to keep an internal resistance of the oxygen sensor at a constant value.

A second object of the present invention is to provide a method for diagnosing malfunction of an oxygen sensor in which malfunction of a limiting current type oxygen sensor is easily diagnosed with a high accuracy.

The first object is achieved by the provision of a method (claim 1) for diagnosing degradation of an oxygen sensor from which a limiting current corresponding to an oxygen concentration is output according to a voltage-current characteristic by applying a sensing voltage placed in a limiting current generating region, comprising the steps of:

changing the sensing voltage applied to the oxygen sensor from a first sensing voltage to a second sensing voltage which is placed outside the limiting current generating region to output a sensing current having a current peak from the oxygen sensor;

detecting a peak current value of the sensing current output from the oxygen sensor;

judging whether or not the peak current value of the sensing current is within a normal range; and diagnosing the oxygen sensor to be degraded in cases where it is judged that the peak current value of the sensing current is not within the normal range.

In the above steps, in a limiting current type oxygen sensor, for example, in cases where a sensing voltage applied to the oxygen sensor is changed from a first sensing voltage having a positive value to a second sensing voltage having a negative value, a sensor current (called a peak current) having a current peak in a negative value direction is generated. In contrast, in cases where a sensing voltage applied to the oxygen sensor is changed from a second sensing voltage having a negative value to a first sensing voltage having a positive value, a sensor current (called a peak current) having a current peak in a positive value direction is generated. In this case, because a value of the peak current (called a peak current value) corresponds to a degradation degree of the oxygen sensor, the degradation of the oxygen sensor can be diagnosed with a high accuracy.

The reason that a peak current value corresponds to a degradation degree of the oxygen sensor is described in detail. An electric function of the limiting current type oxygen sensor is, for example, indicated by an equivalent circuit shown in FIG. 12A. Here, a symbol Rb denotes an internal resistance of a solid electrolyte layer of the oxygen sensor in a resister governing region outside the limiting current generating region, a symbol Rd denotes a resistance at a boundary face between the solid electrolyte layer and an electrode in the limiting current generating region, and a symbol Cd denotes a capacitance of the boundary face. In this case, when pores existing in the electrode are crushed and broken because of the degradation of the oxygen sensor, the resistance Rd increases. However, in cases where a total resistance Zdc=Rb+Rd of the oxygen sensor is feedback-controlled to be set to a target value, the resister Rb is decreased to compensate for the increase of the resister Rd. Therefore, because a current path connecting the resistance Rb and the capacitor Cd is generated just after the change of the sensing voltage, the change of a peak current value is increased. As a result, in cases where the oxygen sensor is degraded in some degree, the peak current value exceeds a degradation judging range, and the judgement that the oxygen sensor is degraded is performed. For example, when the sensing voltage is changed from the first sensing voltage having a positive value Vp to the second sensing voltage having a negative value Vn, the peak current value Io is obtained as follows.

$$Io=Ip-(Vp-Vn)/Rb$$

Accordingly, the degradation of the oxygen sensor can be performed with a high accuracy.

Also, it is applicable that the step of judging whether or not the peak current value of the sensing current is within a normal range comprise the steps of:
waiting by a prescribed time until the sensing current output from the oxygen sensor is converged to a converged current value;
detecting the converged current value of the sensing current; changeably determining the normal range depending on the converged current value; and
judging whether or not the peak current value of the sensing current is within the normal range depending on the converged current value.

In the above steps, as the oxygen sensor is gradually degraded, the resistance Rd increases, a total resistance Zdc=Rb+Rd of the oxygen sensor increases when the total resistance Zdc is not controlled to a constant value, and the converged current value of the sensing current decreases. Therefore, because the normal range depending on the converged current value is changeably determined, the diagnosis of the degradation of the oxygen sensor can be performed with a high accuracy.

Also, it is applicable that the step of judging whether or not the peak current value of the sensing current is within a normal range comprise the steps of:
waiting by a prescribed time until the sensing current output from the oxygen sensor is converged to a converged current value;
detecting the converged current value of the sensing current;
determining a degradation region and a normal region divided by a degradation judging line which is extended in an area defined by the peak current value and the converged current value on condition that a change of an absolute value of the peak current value is larger than another change of an
absolute value of the converged current value;
regarding the normal region as the normal range; and
judging whether or not the peak current value of the sensing current is within the normal range depending on the converged current value.

In the above steps, as the oxygen sensor is gradually degraded, a total resistance Zdc=Rb+Rd of the oxygen sensor increases when the total resistance Zdc is not controlled to a constant value, and the converged current value of the sensing current decreases. In this case, a change of an absolute value of the peak current value is larger than another change of an absolute value of the converged current value. Therefore, because an area defined by the peak current value and the converged current value is divided by a degradation judging line into a degradation region and a normal region on condition that a change of an absolute value of the peak current value is larger than another change of an absolute value of the converged current value, the diagnosis of the degradation of the oxygen sensor can be performed with a high accuracy.

Also, it is applicable that the step of judging whether or not the peak current value of the sensing current is within a normal range comprises the steps of:
detecting an internal resistance of the oxygen sensor;
determining the normal range depending on the internal resistance of the oxygen sensor; and
judging whether or not the peak current value of the sensing current is within the normal range depending on the internal resistance.

In the above steps, because the internal resistance Zdc of the oxygen sensor and the converged current value In satisfies the relationship Zdc=Vn/In, even though the internal resistance Zdc is used in place of the converged current value In, the diagnosis of the degradation of the oxygen sensor can be performed with a high accuracy.

Also, it is applicable that the step of judging whether or not the peak current value of the sensing current is within a normal range comprise the steps of:
detecting an internal resistance of the oxygen sensor;
determining a degradation region and a normal region divided by a degradation judging line which is extended in an area defined by the peak current value and the internal resistance on condition that a change of an absolute value of the peak current value becomes smaller as the internal resistance becomes higher;
regarding the normal region as the normal range; and
judging whether or not the peak current value of the sensing current is within the normal range depending on the internal resistance.

In the above steps, as the oxygen sensor is gradually degraded, a total resistance Zdc=Rb+Rd of the oxygen sensor increases when the total resistance Zdc is not controlled to a constant value. In this case, as the oxygen sensor is gradually degraded, a change of an absolute value of the peak current value becomes smaller. Therefore, because an area defined by the peak current value and the internal resistance is divided by a degradation judging line into a degradation region and a normal region on condition that a change of an absolute value of the peak current value becomes smaller as the internal resistance becomes higher, the diagnosis of the degradation of the oxygen sensor can be performed with a high accuracy.

The first object is also achieved by the provision of an apparatus for diagnosing degradation of an oxygen sensor from which a limiting current corresponding to an oxygen concentration is output according to a voltage-current characteristic by applying a sensing voltage placed in a limiting current generating region, comprising:

voltage changing means for changing the sensing voltage applied to the oxygen sensor from a first sensing voltage to a second sensing voltage which is placed outside the limiting current generating region;

current change detecting means for detecting a change of the sensor current output from the oxygen sensor to which the second sensing voltage is applied by the voltage changing means and detecting a peak current value of the sensing current;

degradation diagnosing means for diagnosing degradation of the oxygen sensor according to the peak current value detected by the current change detecting means by judging whether or not the peak current value of the sensing current is within a normal range;

degradation judging means for judging that the oxygen sensor is degraded in cases where it is judged by the degradation diagnosing means that the peak current value of the sensing current is not within the normal range and outputting a degradation judging signal; and alarming means for displaying the degradation of the oxygen sensor according to the degradation judging signal output from the degradation judging means.

In the above configuration, when a sensing current is detected by the current change detecting means just after a sensing voltage changed by the voltage changing means is applied to the oxygen sensor, a peak current value of the sensing current is detected because a current peak exists in the sensor current. Thereafter, in cases where the peak current value of the sensing current is within a normal range when the degradation of the oxygen sensor is diagnosed by the degradation diagnosing means according to the peak current value, it is judged by the degradation judging means that the oxygen sensor is degraded, and the degradation of the oxygen sensor is displayed by the alarming means to inform a driver of the degradation of the oxygen sensor.

Accordingly, the diagnosis of the degradation of the oxygen sensor can be performed with a high accuracy, and a driver can be informed that the oxygen sensor is degraded.

The second object is achieved by the provision of a method for diagnosing malfunction of an oxygen sensor from which a limiting current corresponding to an oxygen concentration is output according to a voltage-current characteristic by applying a sensing voltage placed in a limiting current generating region, comprising the steps of:

setting a particular sensing voltage at a positive or negative value outside the limiting current generating region;

applying the particular sensing voltage to the oxygen sensor;

detecting a particular sensing current output from the oxygen sensor;

judging whether or not a value of the particular sensing current is within a desired current value range; and informing of a malfunction of the oxygen sensor in cases where the value of the particular sensing current is not within the desired current value range.

In the above steps, when a malfunction exists in the oxygen sensor, an actual value of a sensor current output from the oxygen sensor differs from a desired value expected according to the voltage-current characteristic. In particular, when a particular sensing voltage set at a positive or negative value outside the limiting current generating region is applied to the oxygen sensor, a desired value of the sensor current expected according to the voltage-current characteristic is always positive or negative regardless of the oxygen concentration detected by the oxygen sensor. Therefore, a malfunction diagnosis for the oxygen sensor can be easily performed with a high accuracy by judging whether or not a value of the particular sensing current is within a desired current value range.

BRIEF DESCRIPTION OF THE DRAWINGS

The objects, features and advantages of the present invention will be apparent from the following description taken in conjunction with the accompanying drawings, in which.

DETAIL DESCRIPTION OF THE EMBODIMENTS (First Embodiment)

Hereinafter, a first embodiment in which apparatus and method for diagnosing degradation of an oxygen sensor are used for an air-fuel ratio detecting apparatus of an automobile internal combustion engine is described with reference to drawings.

Figure 1:
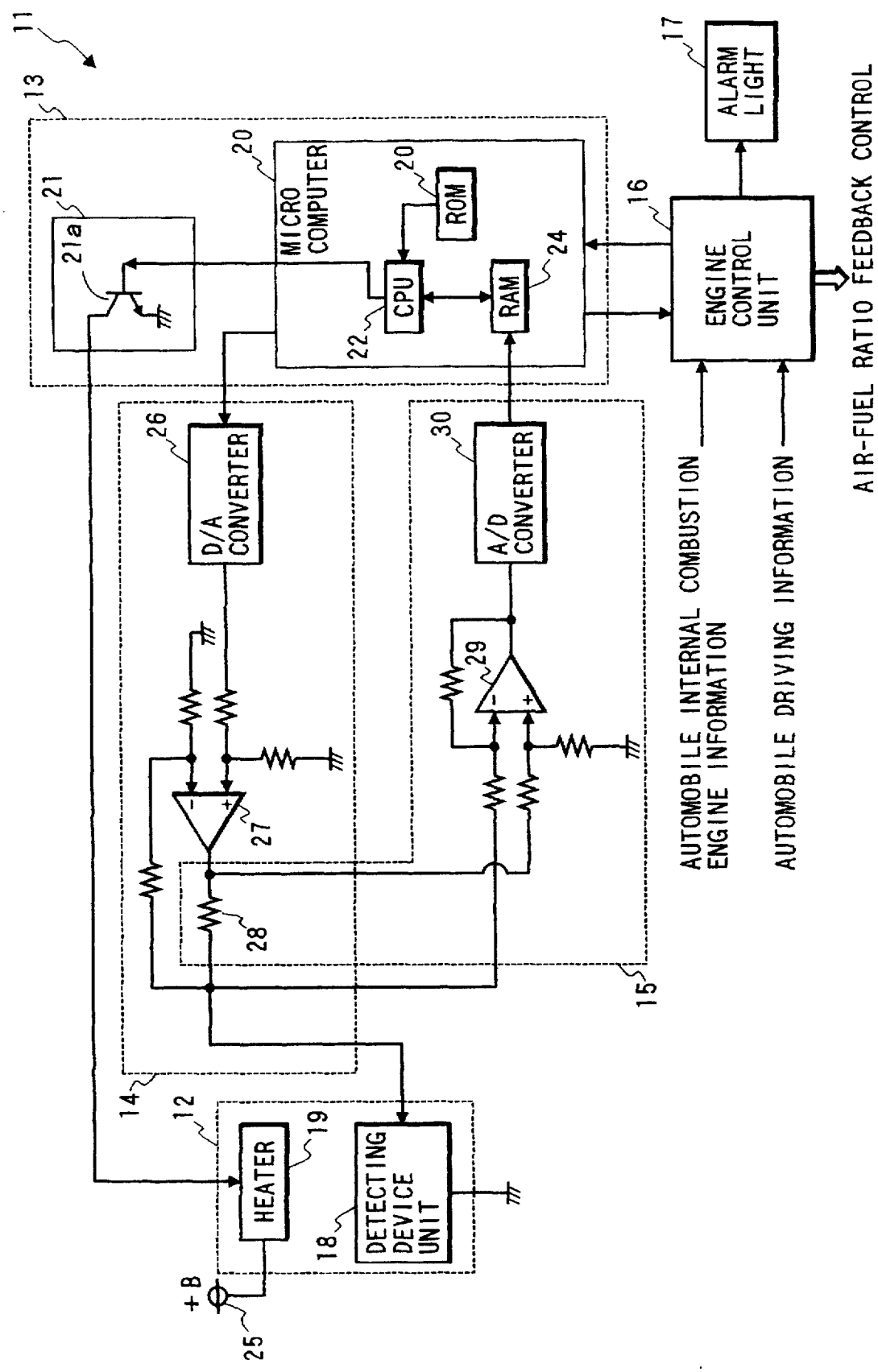
FIG. 1 is a combination of a block-circuit diagram of an air-fuel ratio detecting apparatus according to first, second and third embodiments of the present invention.

FIG. 1 is a combination of a block diagram and a circuit of an air-fuel ratio detecting apparatus according to a first embodiment of the present invention.

As shown in FIG. 1, an air-fuel ratio detecting apparatus 11 comprises an oxygen sensor 12 arranged in an exhaust tube of an automobile for detecting an oxygen concentration or a carbon monoxide (CO) concentration of an exhaust gas of an automobile internal combustion engine, an electronic control unit 13 for calculating an air-fuel ratio of a combustion gas and diagnosing the degradation of the oxygen sensor 12, a voltage applying unit 14 for applying a first sensing voltage Vp or a second sensing voltage Vn to the oxygen sensor 12 according to a voltage control signal output from the electronic control unit 13, an electric current measuring unit 15 for measuring a sensor current generated by the oxygen sensor 12 and outputting the sensor current to the electronic control unit 13 to calculate the air-fuel ratio of the combustion gas and diagnose the degradation of the oxygen sensor 12, an engine control unit 16 for controlling the air-fuel ratio of the combustion gas to an optimum air fuel-ratio according to an air-fuel ratio feedback control by using automobile internal combustion engine information, automobile driving information and the air-fuel ratio determined by the electronic control unit 13 and outputting the automobile internal combustion engine information and the automobile driving information to the electronic control unit 13, and an alarm light 17 for displaying the degradation of the oxygen sensor 12 under control of the electronic control unit 13 and the engine control unit 16 to inform a driver of the degradation of the oxygen sensor 12.

The oxygen sensor 12 comprises a detecting device unit 18 for receiving the sensing voltage Vp or Vn applied by the voltage applying unit 14, detecting the oxygen concentration of the exhaust gas in cases where an air-fuel ratio in a combustion gas is placed in an air-fuel ratio lean region and detecting the CO concentration of the exhaust gas in cases where an air-fuel ratio in a combustion gas is placed in an air-fuel ratio rich region and outputting the sensor current such as a limiting current changing with the oxygen or CO concentration, and a heater 19 for heating the detecting device unit 18 at an active temperature such as about 650° C. or more by receiving a heating current controlled by the electronic control unit 13.

The electronic control unit 13 comprises a micro computer 20 and a heating current adjusting circuit 21 for adjusting the heating current supplied to the detecting device unit 18 under control of the micro computer 20.

The micro computer 20 comprises a central processing unit (CPU) 22 for calculating an air-fuel ratio in the combustion gas according to the sensor current signal output from the electric current measuring unit 15, outputting an air-fuel ratio to the engine control unit 16 to control the air-fuel ratio in the combustion gas to a theoretical air-fuel ratio, outputting an oxygen sensor temperature control signal generated according to the sensor current signal to the heating current adjusting circuit 20 to control the heating current (a function of a heater control means), generating the voltage control signal output to the voltage applying unit 14 to change a sensing voltage applied to the detecting device unit 18 from the first sensing voltage Vp to the second sensing voltage Vn or change the sensing voltage from the second sensing voltage Vn to the first sensing voltage Vp (a function as a voltage changing means), detecting a change of the sensor current output from the detecting device unit 18 according to a change of the sensor current signal (a function of a current change detecting means), diagnosing the degradation of the oxygen sensor 12 according to the change of the sensor current (a function of a degradation diagnosing means), outputting a degradation judging signal to the engine control unit 16 to operate the alarm light 17, detecting an internal resistance of the detecting device unit 18 according to a ratio of the second sensing voltage Vn to a sensor current In output from the detecting device unit 18 (a function of an internal resistance detecting means) and outputting a degradation diagnosing signal to the engine control unit 16 to display the degradation of the oxygen sensor 12 in the alarm light 17, a read only memory (ROM) 23 for storing an arithmetic program used to calculate an air-fuel ratio according to a value of the sensor current generated in the detecting device unit 18, and a random access memory (RAM) 24 for storing a value of the sensor current output from the detecting device unit 18.

The heating current adjusting circuit 21 has a transistor 21a as a switching element, and one end of the heater 19 is connected to a collector terminal of the transistor 21a. Also, the other end of the heater 19 is connected to a buttery source 25. Therefore, when the oxygen sensor temperature control signal is transmitted to a base of the transistor 21a, the transistor 21a is turned on or off, and a value of the heating current is controlled according to a duty ratio control.

In the voltage applying unit 14, the voltage control signal generated in the CPU 22 is changed to an analog signal by a digital-to-analog converter 26, the analog signal is changed to a sensing voltage by an operational amplifier 27, and the sensing voltage is applied to the detecting device unit 18 through a resistor 28. Also, in the current measuring unit 15, a sensor current generated in the detecting device unit 18 by applying the sensing voltage passes through the resistor 28 and is changed to an analog signal by an operational amplifier 29, the analog signal is changed to the sensor current signal by an analog-to-digital converter 30, and the sensor current signal is transmitted to the micro computer 20.

Figure 2:
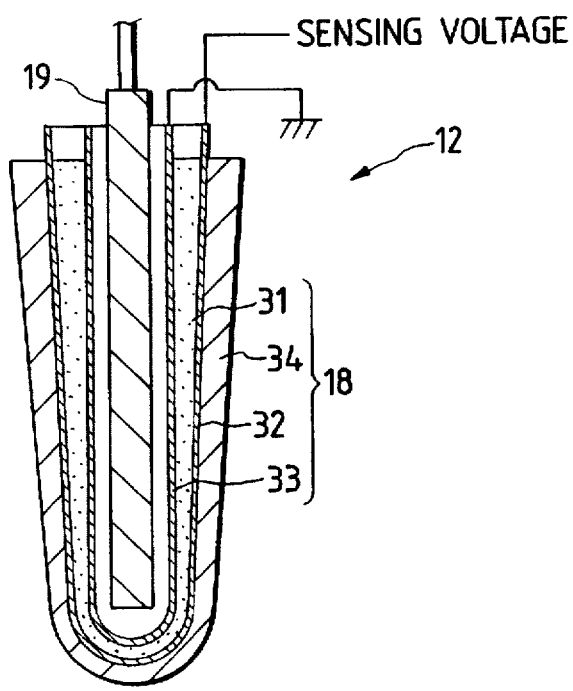
FIG. 2 is a cross sectional view of an oxygen sensor shown in FIG. 1.

FIG. 2 is a cross sectional view of the oxygen sensor 12.

As shown in FIG. 2, the detecting device unit 18 comprises a solid electrolyte layer 31 formed in a U shape cross section, an exhaust gas side electrode layer 32 arranged on an outer surface of the solid electrolyte layer 31, an atmosphere side electrode layer 33 arranged on an inner surface of the solid electrolyte layer 31, and a diffusion resistance layer 34 arranged on an outer surface of the exhaust gas side electrode layer 32. The solid electrolyte layer 31 is made of an oxygen ion conductive oxide sintered body in which CaO, Mgo, $Y_2O_3$, $Yb_2O_3$ or the like is solution-treated in $ZrO_2$, $HfO_2$, $ThO_2$, $Bi_2O_3$ or the like as a stabilizer. The diffusion resistance layer 34 is formed according to a plasma spraying technique and is made of a heat resistance inorganic body such as alumina, magnesia, silica, spinel, mullite or the like. The exhaust gas side electrode layer 32 and the atmosphere side electrode layer 33 are made of nobel metal having a high catalytic activity such as platinum and are placed on both surfaces of the solid electrolyte layer 31 as a porous chemical metal plating. The exhaust gas side electrode layer 32 has an area ranging from 10 to 100 $mm^2$ and a thickness ranging from 0.5 to 2.0 μm. The atmosphere side electrode layer 33 has an area of 10 $mm^2$ or more and a thickness ranging from 0.5 to 2.0 μm. The solid electrolyte layer 31 is equivalent to an oxygen concentration detecting device.

The heater 19 is placed in a central portion of the oxygen sensor 12 and is surrounded by the atmosphere side electrode layer 33 to heat the atmosphere side electrode layer 33, the solid electrolyte layer 31, the exhaust gas side electrode layer 32 and the diffusion resistance layer 34. A heating capacity of the heater 19 is sufficient to activate the detecting device unit 18.

In the above configuration of the oxygen sensor 12, when a sensing voltage is applied to the exhaust gas side electrode layer 32, a concentration electromotive force is generated at a theoretical air-fuel ratio point by the detecting device unit 18. Therefore, when a first sensing voltage Vp is applied to the exhaust gas side electrode layer 32, a limiting current of which a value corresponds to an oxygen concentration of an exhaust gas is generated by the detecting device unit 18 in cases where an air-fuel ratio in a combustion gas is placed in an air-fuel ratio lean region. Also, in cases where an air-fuel ratio in a combustion gas is placed in an air-fuel ratio rich region, an unburned gas remains in an exhaust gas as a carbon monoxide (CO), a CO concentration of the exhaust gas linearly changes with an air-fuel ratio in a combustion gas, and a limiting current of which a value corresponds to the CO concentration of the exhaust gas is generated by the detecting device unit 18. In this case, a value of the limiting current corresponding to the oxygen or CO concentration is determined by the area of the exhaust gas side electrode layer 32, the thickness of the diffusion resistance layer 34, a porous ratio and an average porous diameter in the exhaust gas side electrode layer 32 and a porous ratio and an average porous diameter in the atmosphere side electrode layer 33.

A voltage-current characteristic in the oxygen sensor 12 is described in detail with reference to FIG. 3.

Figure 3:
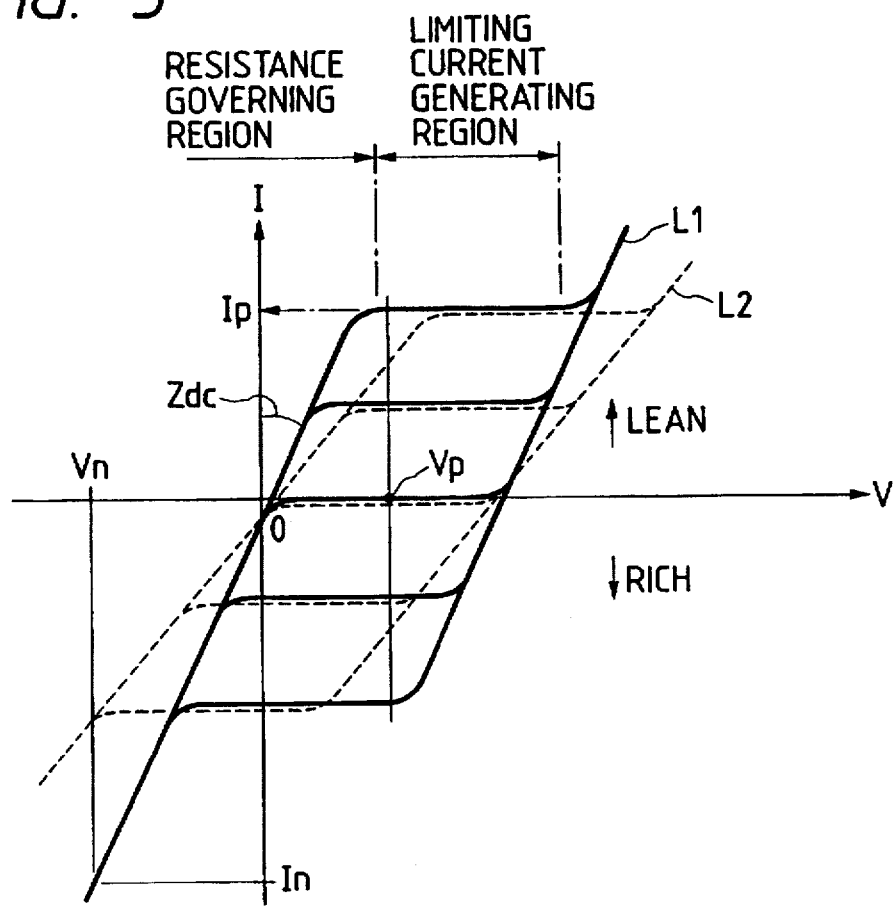
FIG. 3 shows a voltage-current characteristic in the oxygen sensor.

As shown in FIG. 3, a limiting current generating region, in which a value of a sensor current flowing the solid electrolyte layer 31 is almost constant even though a sensing voltage applied to the solid electrolyte layer 31 through the exhaust gas side electrode layer 32 changes, is indicated by a characteristic line L1 (expressed by a solid line) corresponding to a particular air-fuel ratio. That is, the characteristic line L1 in the limiting current generating region is parallel to a voltage axis, and the limiting current generating region is also called an excess voltage governing region. Therefore, a value of the limiting current is specified in the limiting current generating region. A value of the limiting current linearly changes with an air-fuel ratio. That is, the value of the limiting current increases as the air-fuel ratio shifts to the air-fuel ratio lean region, and the value of the limiting current decreases as the air-fuel ratio shifts to the air-fuel ratio rich region.

Also, a resistance governing region exists at a region in which a sensing voltage is lower than that in the limiting current generating region, and a slope of the characteristic line L1 in the resistance governing region is determined by an internal resistance of the solid electrolyte layer 31. In this case, the internal resistance of the solid electrolyte layer 31 changes with a temperature of the solid electrolyte layer 31. Therefore, when the temperature of the detecting device unit 12 is lowered, the internal resistance of the solid electrolyte layer 31 increases, and a slope of a characteristic line indicating the voltage-current characteristic is lowered. For example, the voltage-current characteristic is indicated by a characteristic line L2 (expressed by a dotted line) corresponding to a temperature of the detecting device unit 12 lower than that for the characteristic line L1. However, even though the temperature of the detecting device unit 12 changes, a value of the limiting current is almost constant. Therefore, a value of the limiting current indicated in by the characteristic line L2 is almost the same as that indicated in by the characteristic line L1.

In the above configuration of the air-fuel ratio detecting apparatus 11 and the above function of the oxygen sensor 12, an operation performed in the air-fuel ratio detecting apparatus 11 is described.

Figure 4:
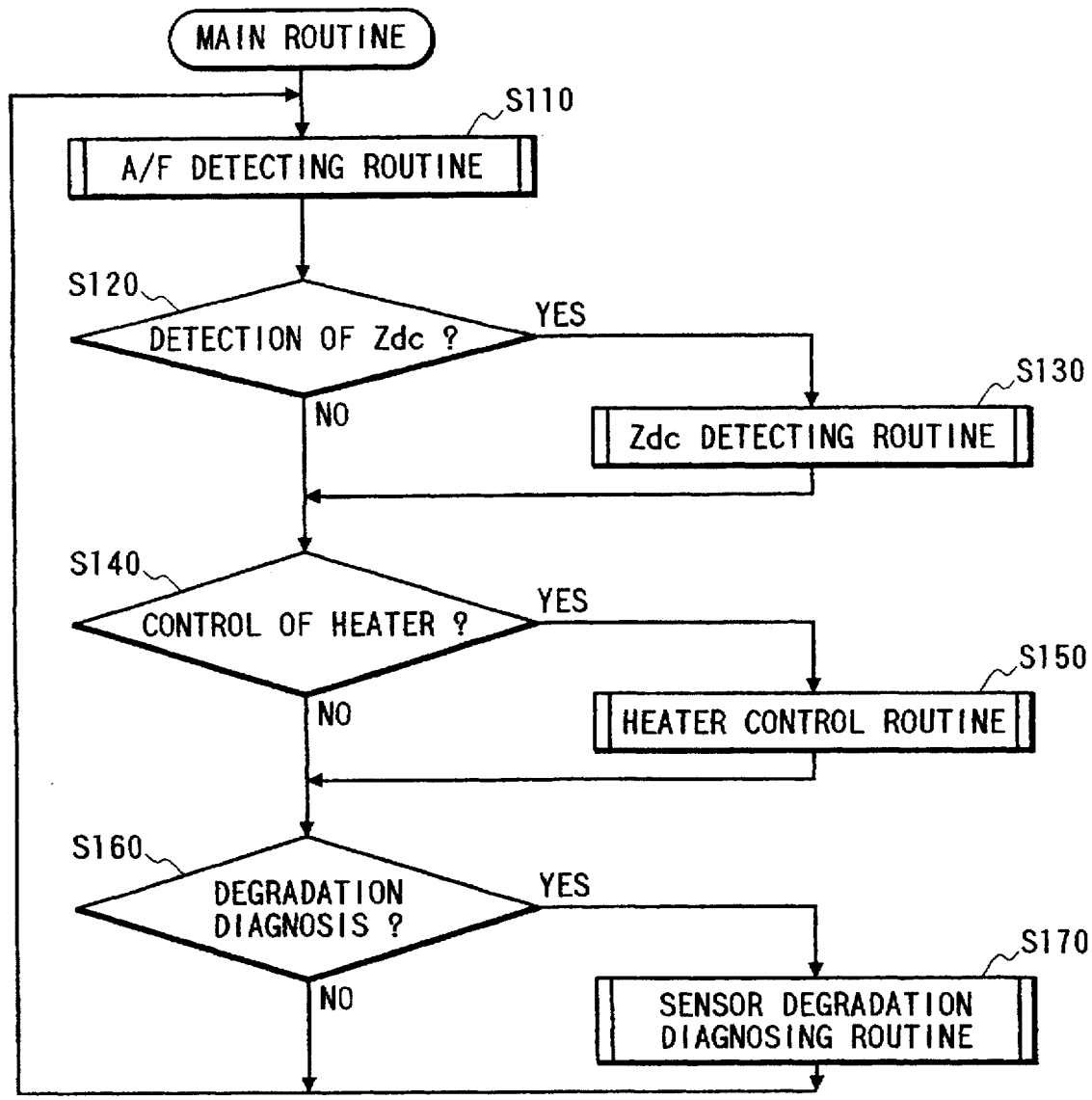
FIG. 4 is a flow chart of a main routine performed by a CPU shown in FIG. 1.

FIG. 4 is a flow chart of a main routine performed by the CPU 22 of the micro computer 20 according to a first embodiment. This main routine is performed by the CPU 22 every several milli-seconds (ms).

As shown in FIG. 4, when the main routine is started, an air-fuel ratio detecting routine is performed by the CPU 22 in a step S110. In a normal operation, only the air-fuel ratio detecting routine is performed every several milli-seconds (ms).

Figure 5:
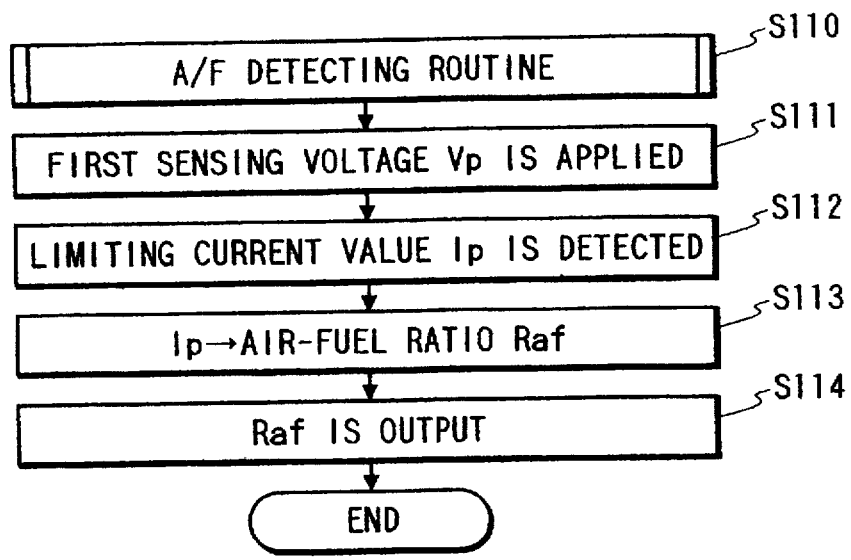
FIG. 5 is a flow chart of an air-fuel ratio detecting routine performed by the CPU according to the first embodiment.

FIG. 5 is a flow chart of the air-fuel ratio detecting routine performed by the CPU 22.

Figure 9:
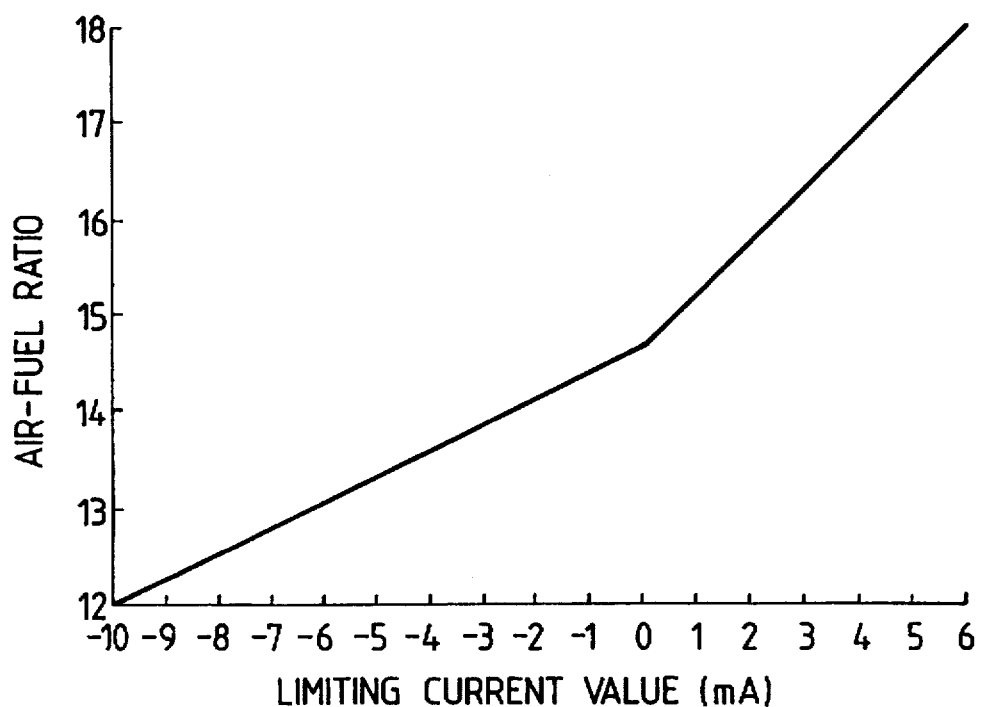
FIG. 9 shows a relationship between a limiting current value Ip and an air-fuel ratio.

As shown in FIG. 5, in the air-fuel ratio detecting routine, a first sensing voltage vp having a positive value is initially applied to the detecting device unit 18 of the oxygen sensor 12 in a step Sill. As shown in FIG. 3, the first sensing voltage Vp is determined on condition that a value Ip of the limiting current can be detected regardless of the increase and decrease of the air-fuel ratio changing in a desired detection range. For example, when an internal resistance Zdc of the solid electrolyte layer 31 is 30 Ω and the air-fuel ratio ranges from 12 to 18, the first sensing voltage Vp ranging from 0.3 to 0.5 V is selected. Thereafter, a value Ip of the limiting current flowing the solid electrolyte layer 31 is detected in a step S112 when the first sensing voltage VP is applied. Thereafter, the value Ip of the limiting current is converted into an air-fuel ratio Raf in a step S113 according to the relationship between the limiting current and the air-fuel ratio shown in FIG. 9 which is stored in the ROM 23 as an arithmetic program. Thereafter, the air-fuel ratio Raf calculated is output to the engine control unit 16 in a step S114, and the air-fuel ratio detecting routine is finished.

Thereafter, as shown in FIG. 4, it is judged in a step S120 whether or not the internal resistance Zdc of the solid electrolyte layer 31 is to be detected. In this case, when a temperature of the exhaust gas suddenly changes, the detection of the internal resistance Zdc is required. That is, automobile internal combustion engine information such as the number of rotations in the automobile internal combustion engine, a pressure of an intake pipe, a volume of an intake air, a volume of an exhaust gas or the like suddenly changes, it is judged in the step S120 that the detection of the internal resistance Zdc is required. In this embodiment, the judgement in the step S120 is performed after the step 110. However, it is applicable that the judgement be periodically performed, for example, every one second. In this case, it is not required to input the automobile internal combustion engine information to the CPU 22 through the engine control unit 16. In cases where the detection of the internal resistance Zdc is required in the step S120, an internal resistance detecting routine is performed in a step S130.

Figure 6:
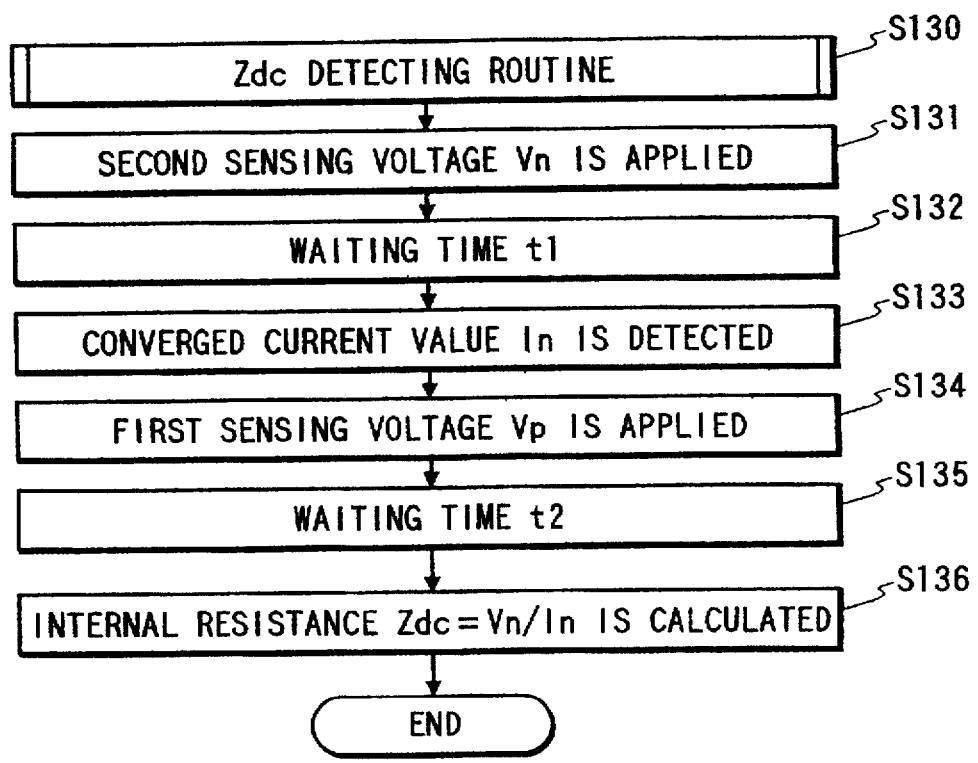
FIG. 6 is a flow chart of an internal resistance detecting routine performed by the CPU 22 according to the first embodiment.
Figure 10:
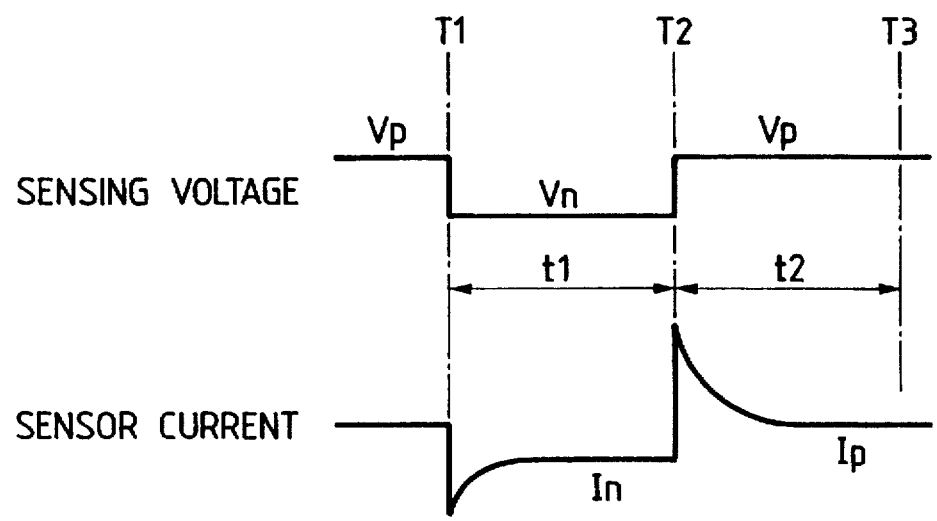
FIG. 10 is a time chart of a sensing voltage and a sensing current used in an internal resistance detecting routine performed by the CPU according to the first and third embodiments.

FIG. 6 is a flow chart of the internal resistance detecting routine performed by the CPU 22, and FIG. 10 is a time chart of a sensing voltage applied to the oxygen sensor 12 and a sensing current output from the oxygen sensor 12.

As shown in FIG. 6, the sensing voltage applied to the oxygen sensor 12 is changed to a second sensing voltage Vn having a negative value, and the second sensing voltage vn is applied to the detecting device unit 18 of the oxygen sensor 12 in a step S131. As shown in FIG. 3, the second sensing voltage Vn is not placed in the limiting current generating region but placed in the resistance governing region and ranges from −0.3 to −1 V. Thereafter, the detection of the sensor current output from the detecting device unit 18 is waited by a first waiting time t1 in a step S132. That is, as shown in FIG. 10, when the sensing voltage applied to the oxygen sensor 12 is changed from the first sensing voltage Vp to the second sensing voltage Vn at a time T1, a sensor current having a current peak is generated just after the change of the sensing voltage to sharply change a value of the sensor current, and a value of the sensor current is converged to a value In according to a static characteristic of the sensor current. The value In is called a converged current value In. Therefore, the detection of the sensor current is waited by the first waiting time t1 which is required to perfectly converge the value of the sensor current. The first waiting time t1 ranges from several tens of milli-seconds to several hundreds of milli-seconds. After the first waiting time t1, the converged current value In is detected by the CPU 22 in a step S133 and is stored in the RAM 24.

Thereafter, the sensing voltage is changed to the first sensing voltage vp, and the first sensing voltage vp is applied to the oxygen sensor 12 in a step S134. Thereafter, the detection of the sensor current output from the detecting device unit 18 is waited by a second waiting time t2 in a step S135. That is, as shown in FIG. 10, when the sensing voltage applied to the oxygen sensor 12 is changed from the second sensing voltage Vn to the first sensing voltage Vp at a time T2, a sensor current having a current peak is generated just after the change of the sensing voltage, and a value of the sensor current is converged to a limiting current value Ip according to the static characteristic of the sensor current. The second waiting time t2 ranges from several tens of milli-seconds to several hundreds of milli-seconds. After the second waiting time t2, the limiting current value Ip is detected, and the internal resistance Zdc=Vn/In of the solid electrolyte layer 31 is calculated by the CPU 22 at a time T3 in a step S136.

Accordingly, because the characteristic line shown in FIG. 3 passes through the origin regardless of the air-fuel ratio and straightly extends in the resistance governing region and because the converged current value In is detected after the sensor current value is sufficiently converged, the internal resistance Zdc=Vn/In of the solid electrolyte layer 31 can be obtained with a high accuracy.

After the internal resistance detecting routine is finished, as shown in FIG. 4, it is judged in a step S140 whether or not a heater control is to be performed. In this case, in the same manner as in the step S120, when automobile internal combustion engine information such as the number of rotations in the automobile internal combustion engine, a pressure of an intake pipe, a volume of an intake air, a volume of an exhaust gas or the like suddenly changes, it is judged in the step S140 that the heater control is required. In this embodiment, the judgement in the step S140 is performed after the step 120 or 130. However, it is applicable that the judgement be periodically performed, for example, every one second. In this case, it is not required to input the automobile internal combustion engine information to the CPU 22 through the engine control unit 16. In cases where the heater control is required in the step S140, a heater control routine is performed in a step S150.

In the heater control routine according to this embodiment, a value of the heating current supplied to the heater 19 is controlled according to a duty ratio control based on a pulse width modulation (PCM). In this case, a control duty DC supplied to the heater 19 is calculated according to following equations (1), (2) and (3).

$$GP=KP*(Zdc-ZdcT) \quad (1)$$

$$GI=GIi-1+KI*(Zdc-ZdcT) \quad (2)$$

$$DC=GP+GI \quad (3)$$

Here, a symbol GP denotes a proportional term, a symbol GI denotes an integrating term, a symbol KP denotes a proportional constant, a symbol KI denotes an integrating constant, and a symbol ZdcT denotes a target internal resistance value of the solid electrolyte layer 31.

Figure 7:
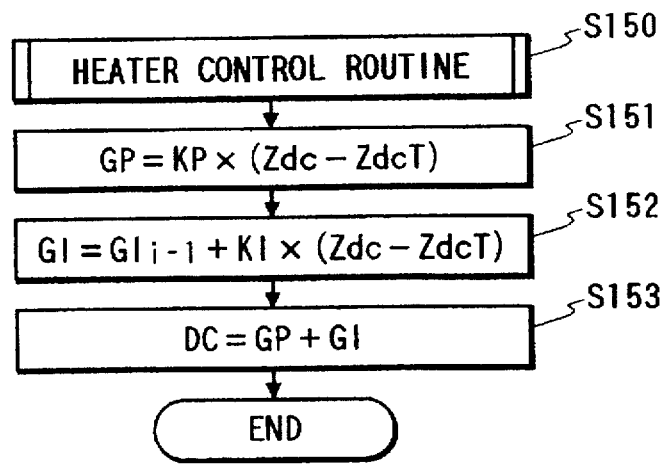
FIG. 7 is a flow chart of a heater control routine performed by the CPU according to the first embodiment.

FIG. 7 is a flow chart of the heater control routine performed by the CPU 22.

As shown in FIG. 7, the proportional term GP is calculated according to the equation (1) in a step S151 by using a deviation of the internal resistance Zdc obtained in the internal resistance detecting routine (step S130) from the target internal resistance value ZdcT. Thereafter, the integrating term GI is calculated according to the equation (2) in a step S152 by using the deviation of the internal resistance Zdc from the target internal resistance value ZdcT. Thereafter, the control duty DC is calculated according to the equation (3) in a step S153, and the heater control routine is finished. Thereafter, an oxygen sensor temperature control signal indicating the control duty DC is transmitted to the heating current adjusting circuit 21 to control the transistor 21a, and the heating current is supplied to the heater 19 to control the internal resistance value Zdc to the target internal resistance value ZdcT according to a feedback control.

In this embodiment, a proportional integral (PI) control for the heater 19 is performed. However, it is applicable that a proportional integral and differential (PID) control or an integral (I) control for the heater 19 be performed.

Thereafter, as shown in FIG. 4, it is judged in a step S160 whether or not the diagnosis of the degradation of the oxygen sensor 12 is performed. In this case, the judgement is performed according to a piece of driving information such as a running distance of an automobile. Also, it is applicable that the judgement be performed according t o an elapsed time after a previous judgement. In cases where the diagnosis of the degradation of the oxygen sensor is required, a sensor degradation diagnosing routine is performed in a step S170.

Figure 8:
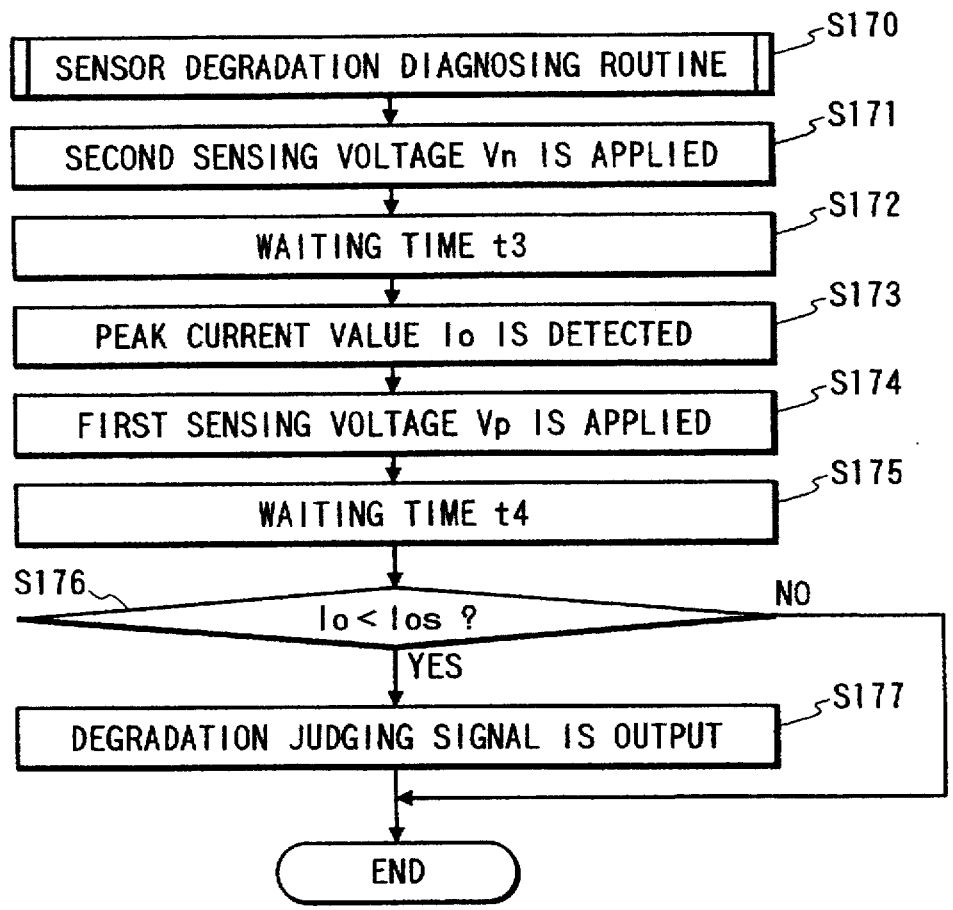
FIG. 8 is a flow chart of a sensor degradation diagnosing routine performed by the CPU according to the first embodiment.

FIG. 8 is a flow chart of the sensor degradation diagnosing routine performed by the CPU 22 according to the first embodiment.

As shown in FIG. 8 the sensing voltage applied to the oxygen sensor 12 is changed to a second sensing voltage Vn having a negative value, and the second sensing voltage Vn is applied to the detecting device unit 18 of the oxygen sensor 12 in a step S171. As shown in FIG. 3, the second sensing voltage Vn is not placed in the limiting current generating region but placed in the resistance governing region and ranges from −0.3 to −1 V in the same manner as that in the internal resistance detecting routine. Thereafter, the detection of the sensor current output from the detecting device unit 18 is waited by a third waiting time t3 in a step S172. In this case, the third waiting time t3 is considerably shorter than the first waiting time t1 of the internal resistance detecting routine (t3<t1). For example, the third waiting time t3 is shorter than several tens of milli-seconds. After the third waiting time t3, a value Io of the sensor current is detected in a step S173. Because the sensor current still forms a peak, the value Io is called a peak current value. The peak current value Io is stored in the RAM 24.

Thereafter, the sensing voltage applied to the oxygen sensor 12 is returned to the first sensing voltage Vp in a step S174, and the detection of the sensor current output from the detecting device unit 18 is waited by a fourth waiting time t4 in a step S175. The fourth waiting time t4 is required to converge a peak value of the sensor current occurring at a sensing voltage changing operation. Therefore, the fourth waiting time t4 ranges from several tens of milli-seconds to several hundreds of milli-seconds and is the same as the second waiting time t2 (t4=t2).

Thereafter, it is judged in a step S176 whether or not the peak current value Io is lower than a prescribed degradation judging value Ios. In this case, the degradation judging value Ios depends on a degradation judging standard of each air-fuel ratio detecting apparatus. In this embodiment, the degradation judging value Ios is set to a value several mA lower than the peak current value Io obtained when the oxygen sensor 12 normally functions. In cases where the peak current value Io is equal to or higher than the degradation judging value Ios (Io≧Ios), it is judged that the oxygen sensor 12 normally functions, and the sensor degradation diagnosing routine is finished. In contrast, in cases where the peak current value Io is lower than the degradation judging value Ios (Io<Ios), it is judged that the oxygen sensor 12 is degraded, and the procedure proceeds to a step S177. In the step S177, a degradation judging signal is transmitted from the CPU 22 to the engine control unit 16, and the sensor degradation diagnosing routine is finished. In cases where the degradation judging signal is transmitted to the engine control unit 16, the alarm light 17 is operated to inform a user of the degradation of the oxygen sensor 12, and an air-fuel ratio feedback control performed by the engine control unit 16 to control the air-fuel ratio of the combustion gas to an optimum air-fuel ratio is stopped.

Figure 11:
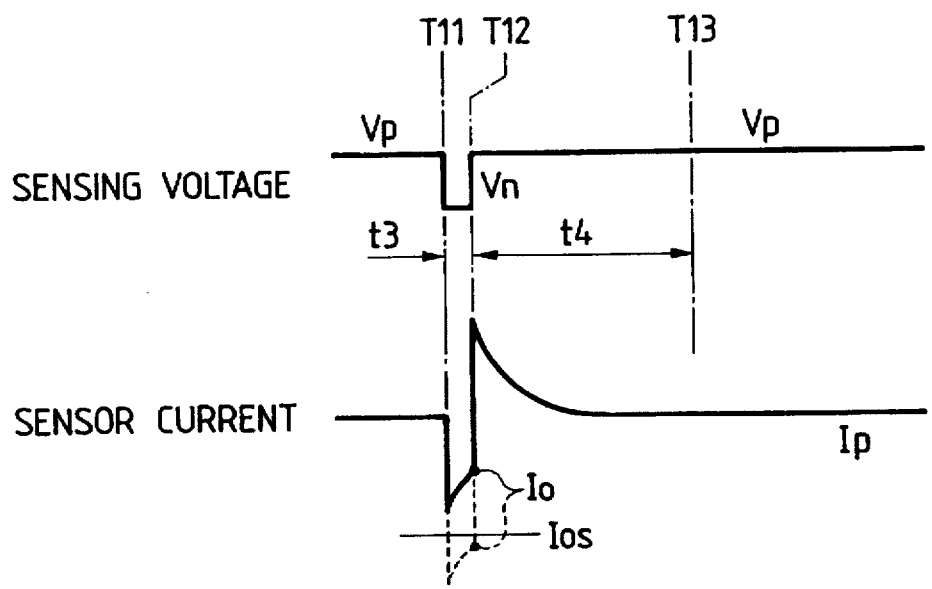
FIG. 11 is a time chart of a sensing voltage and a sensing current used in a sensor degradation diagnosing routine shown in FIG. 8.

The sensor degradation diagnosing routine shown in FIG. 8 is concretely described by referring a time chart shown in FIG. 11.

As shown in FIG. 11, when the sensing voltage applied to the detecting device unit 18 of the oxygen sensor 12 is changed from the first sensing voltage Vp to the second sensing voltage Vn at a time T11, a sensor current having a current peak is output from the detecting device unit 18. That is, a value of the sensor current is immediately dropped and gradually increase. After the third waiting time t3 is elapsed, the peak current value Io is detected at a time T12, and the sensing voltage applied to the oxygen sensor 12 is changed from the second sensing voltage Vn to the first sensing voltage Vp at the same time T12. In this case, because the third waiting time t3 is considerably shorter than the first waiting time t1, a value of the sensor current is not converged to the converged current value In, and Io<In is satisfied. Thereafter, when the fourth waiting time t4 is elapsed, the limiting current value Ip is detected, and the judgement whether or not the oxygen sensor 12 is degraded is performed by using the peak current value Io. In cases where the peak current value Io is equal to or higher than the degradation judging value Ios (Io≧Ios) as is indicated by a solid line, it is judged that the oxygen sensor 12 normally functions. In contrast, in cases where the peak current value Io is lower than the degradation judging value Ios (Io<Ios) as is indicated by a dotted line, it is judged that the oxygen sensor 12 is degraded.

The reason that the peak current value Io is lowered when the oxygen sensor 12 is degraded is described with reference to FIGS. 12A and 12B.

Figure 12A:
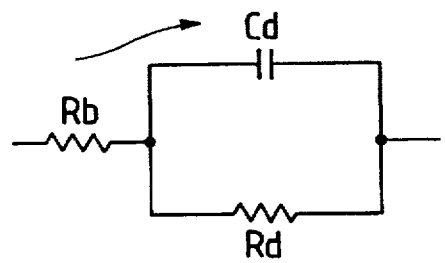
FIG. 12A shows an equivalent circuit of a detecting device unit shown in FIG. 1.
Figure 12B:
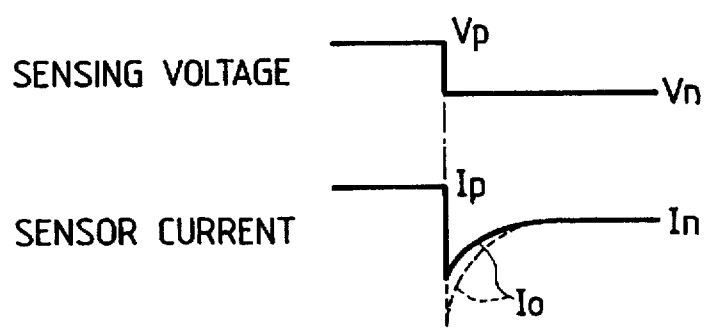
FIG. 12B shows a waveform of a sensing voltage and a waveform of a sensor current generated in the equivalent circuit shown in FIG. 12A.

FIG. 12A shows an equivalent circuit of the detecting device unit 18, and FIG. 12B shows a waveform of a sensing voltage applied to the equivalent circuit and a waveform of a sensor current flowing the equivalent circuit.

In FIG. 12A, a resistance Rb of a resistor Rb corresponds to the internal resistance of the solid electrolyte layer 31 in the resister governing region, a resistance Rd of a resister Rd corresponds to a sum of a first resistance at a boundary face between the solid electrolyte layer 31 and the exhaust gas side electrode layer 32 and a second resistance at a boundary face between the solid electrolyte layer 31 and the atmosphere side electrode layer 33 in the limiting current generating region, and a capacitance Cd of a capacitor Cd corresponds to a sum of capacitances of the boundary faces. In this case, the internal resistance Zdc of the solid electrolyte layer 31 satisfies a relationship Zdc=Rb+Rd. Because a sensor current passes through the resistor Rb and the capacitor Cd just after a change operation of the sensing voltage, the peak current value Io is determined by the resistor Rb as follows.

$$Io=Ip(Vp-Vn)/Rb \quad (4)$$

Also, the degradation of the oxygen sensor 12 is caused as follows. That is, the exhaust gas side electrode layer 32 and the atmosphere side electrode layer 33 which are made of platinum formed in a porous shape are degraded, pores existing in the electrode layers 32 and 33 are crushed and broken, and the passage of oxygen through the electrode layers 32 and 33 is disturbed. In this case, because the resistance Rd indicating the sum of those at the boundary faces is increased, the heater control shown in FIG. 7 is performed to control the internal resistance Zdc of the solid electrolyte layer 31 to a constant value. That is, the heating current supplied to the heater 19 is increased to increase the temperature of the detecting device unit 18, and the resistance Rb indicating the internal resistance of the detecting device unit 18 is reduced. Therefore, even though the internal resistance Zdc=Rb+Rd of the solid electrolyte layer 31 in a degraded oxygen sensor is the same as that in the oxygen sensor 12 normally functioning, the resistance Rb is lowered when the oxygen sensor 12 is degraded, and the peak current value Io is decreased (refer to the equation (4)).

Accordingly, the degradation of the oxygen sensor 12 can be easily diagnosed by observing the peak current value Io when the sensing voltage applied to the oxygen sensor 12 is changed, and the degradation of the oxygen sensor 12 can be judged with a high accuracy by detecting the decrease of the peak current value Io.

Also, because it is desired to reduce automobile emissions as much as possible in a recent air-fuel ratio control system, the control of the heating current supplied to the heater 19 is desired to keep the internal resistance Zdc at a constant value. Therefore, the apparatus and method for diagnosing the degradation of the oxygen sensor 12 according to the first embodiment can be useful for the recent air-fuel ratio control system in which the heater control is performed.

Also, the first or second waiting time t1 or t2 required to wait for the convergence of the sensor current just after the change of the sensing voltage applied to the oxygen sensor 12 ranges from several tens of milli-seconds to several hundreds of milli-seconds. However, the third waiting time t3 required to detect the peak current value Io for the purpose of diagnosing the degradation of the oxygen sensor 12 is within several tens of milli-seconds. Therefore, a time required to diagnose the degradation of the oxygen sensor 12 can be shortened.

(Second Embodiment)

Though a value of the heating current supplied to the heater 19 is controlled by the micro computer 20 according to a feedback control to make the internal resistance Zdc of the solid electrolyte layer 31 agreeing with the target internal resistance ZdcT in the first embodiment, an open control is adopted for the value of the heating current in the second embodiment. That is, even though the internal resistance Zdc of the solid electrolyte layer 31 changes, the heating current (or the control duty DC) is set to a constant value in the second embodiment by a function of an open control circuit (not shown).

Figure 13:
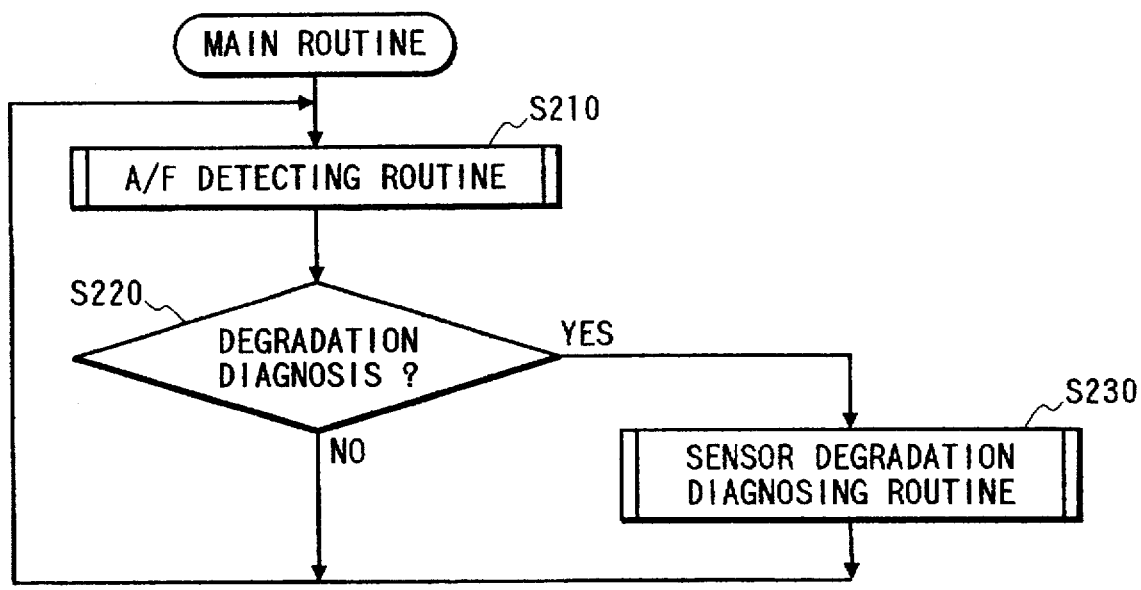
FIG. 13 is a flow chart of a main routine performed by the CPU according to a second embodiment.

FIG. 13 is a flow chart of a main routine performed by the CPU 22 of the micro computer 20 according to the second embodiment.

As shown in FIG. 13, when the main routine is started, an air-fuel ratio detecting routine is performed by the CPU 22 in a step S210 in the same manner as in the step S110 shown in FIGS. 4 and 5. Thereafter, it is judged in a step S220 whether or not the diagnosis of the degradation of the oxygen sensor 12 is performed. The judgement is performed in the same manner as in the step S160. In cases where the diagnosis of the degradation of the oxygen sensor is required, a sensor degradation diagnosing routine is performed in a step S230.

Figure 14:
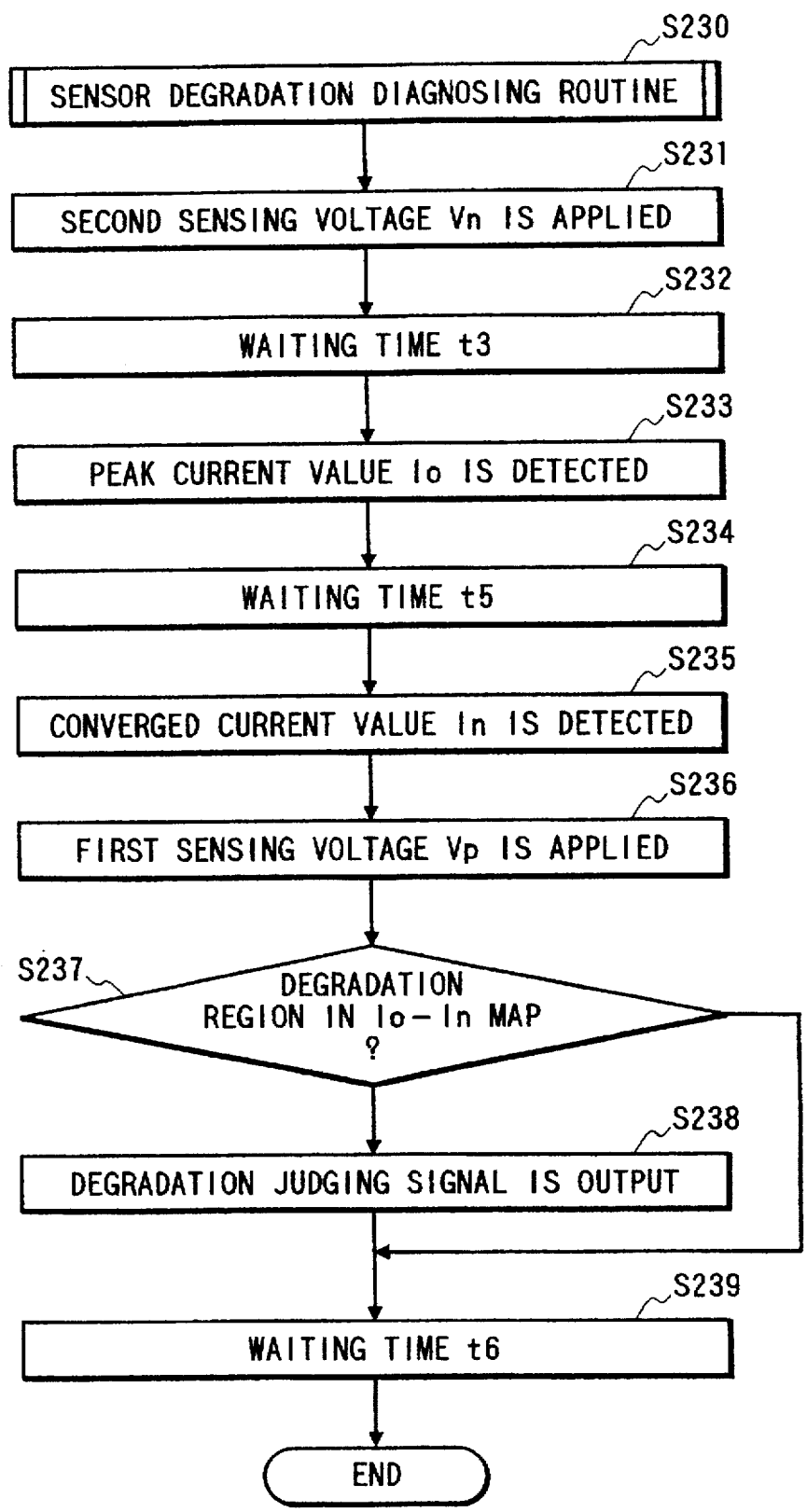
FIG. 14 is a flow chart of a sensor degradation diagnosing routine performed by the CPU according to the second embodiment.

FIG. 14 is a flow chart of the sensor degradation diagnosing routine performed by the CPU 22 according to the second embodiment.

As shown in FIG. 14, steps S231 to S233 are performed in the same manner as the steps S171 to S173. That is, the second sensing voltage Vn having a negative value is applied to the detecting device unit 18 in the step S231, the detection of the sensor current is waited by the third waiting time t3 in a step S232, and a peak current value Io is detected in the step S233 and is stored in the RAM 24. After the detection of the peak current value Io, the detection of the sensor current is waited by a fifth waiting time t5 ranging from several tens of milli-seconds to several hundreds of milli-seconds in a step S234, and a converged current value In of the sensor current is detected in a step S235 and is stored in the RAM 22. Here, the fifth waiting time t5 is required to perfectly converge the value of the sensor current just after a changing operation of the sensing voltage applied to the detecting device unit 18. Thereafter, the sensing voltage is returned to the first sensing voltage Vp, and the first sensing voltage Vp is applied to the detecting device unit 18 in a step S236.

Figure 16:
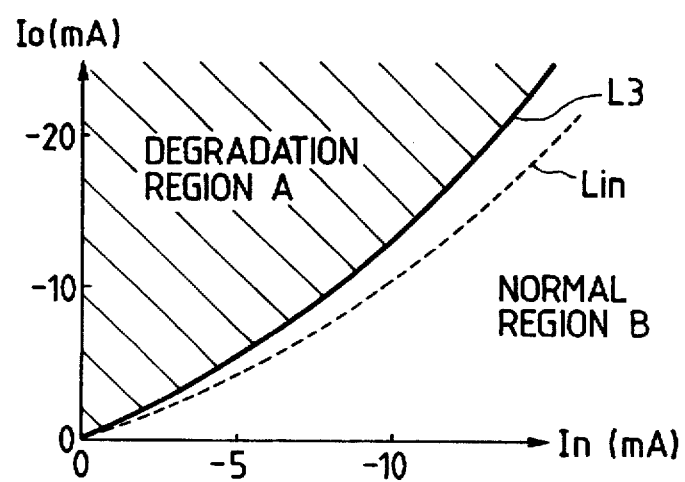
FIG. 16 shows an In-Io map indicating a degradation region based on a relationship between a converged current value (In) and a peak current value (Io)

Thereafter, the judgement whether or not the oxygen sensor 12 is degraded is performed in a step S237 according to an Io-In map which is stored in the ROM 23 in advance and indicates the relationship between the peak current value Io and the converged current value In. That is, as shown in FIG. 16, a whole region in the Io-In map is divided by a degradation judging line L3 into a degradation region A and a normal region B, the degradation judging line L3 passes through the origin, and a slope of the degradation judging line L3 becomes high as the degradation judging line L3 extends toward a negative direction of the converged current value In.

In cases where an operation position (In, Io) which is determined by the peak current value Io obtained in the step S233 and the converged current value In obtained in the step S235 is placed in the normal region B, it is judged by the CPU 22 that the oxygen sensor 12 normally functions, and the procedure proceeds to a step S239. In contrast, in cases where the operation position (In, Io) is placed in the degradation region A, it is judged by the CPU 22 that the oxygen sensor 12 is degraded, and the procedure proceeds to a step S238.

In the step S238, a degradation judging signal is transmitted from the CPU 22 to the engine control unit 16. Thereafter, the detection of the value of the sensor current is waited by a sixth waiting time t6 ranging from several tens of milli-seconds to several hundreds of milli-seconds in the step S239, the limiting current value Ip is detected, and the sensor degradation diagnosing routine is finished. In cases where the degradation judging signal is transmitted to the engine control unit 16, the alarm light 17 is operated to inform a user of the degradation of the oxygen sensor 12, and an air-fuel ratio feedback control performed by the engine control unit 16 to control the air-fuel ratio of the combustion gas to an optimum air-fuel ratio is stopped.

The reason that the degradation region A and the normal region B are separated from each other by the degradation judging line L3 of which the slope becomes high as the degradation judging line L3 extends toward a negative direction of the converged current value In is described. Because the open control is adopted for the value of the heating current in the second embodiment, when the oxygen sensor 12 is degraded in some degree, the internal resistance Zdc of the solid electrolyte layer 31 increases, an absolute value of the converged current value In decreases at a first changing rate, and an absolute value of the peak current value Io decreases at a second changing rate. In this case, the second changing rate in the peak current value Io is higher than the first changing rate in the converged current value In. That is, a ratio of a changing degree of the peak current value Io to a changing degree of the converged current value In increases as a degradation degree of the oxygen sensor 12 becomes high. Therefore, the slope of the degradation judging line L3 is set to become high as the degradation judging line L3 extends toward a negative direction of the converged current value In.

Figure 15:
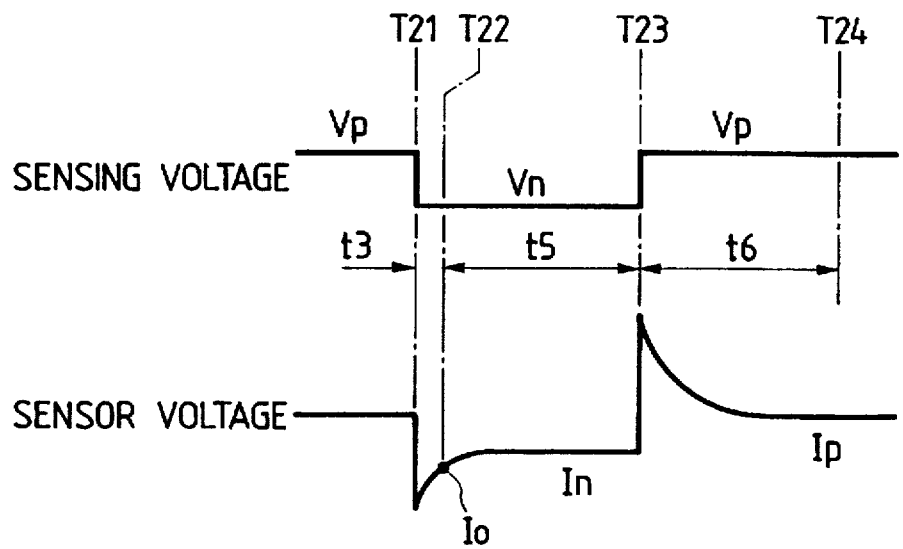
FIG. 15 is a time chart of a sensing voltage and a sensing current used in a sensor degradation diagnosing routine according to the second embodiment.

The sensor degradation diagnosing routine is concretely described by referring to a time chart shown in FIG. 15.

As shown in FIG. 15, the sensing voltage applied to the detecting device unit 18 is changed from the first sensing voltage Vp to the second sensing voltage Vn at a time T21. Thereafter, when the third waiting time t3 is elapsed, the peak current value Io is detected at a time T22. Thereafter, when the fifth waiting time t5 is elapsed, the sensing voltage is returned to the first sensing voltage Vp at a time T23, and the judgement whether or not the oxygen sensor 12 is degraded is performed by using the peak current value Io and the converged current value In. Thereafter, when the sixth waiting time t6 is elapsed, the sensor degradation diagnosing routine is finished at a time T24.

The degradation judging line L3 of the Io-In map shown in FIG. 16 is set as follows. That is, an initial characteristic of the oxygen sensor 12 is measured, and an initial relationship between an initial peak current value Ioi and an initial converged current value Ini corresponding to the initial characteristic is drawn in the Io-In map. The initial relationship is indicated by an initial characteristic line Lin expressed by a dotted line in FIG. 16. Thereafter, the degradation judging line L3 is determined by shifting the initial characteristic line Lin toward a negative value direction of the peak current value Io by several % of the initial peak current value Ioi. A difference between the degradation judging line L3 and the initial characteristic line Lin depends on a degradation degree of the oxygen sensor 12 that a driver desires to judge as a degraded oxygen sensor. For example, when the driver desires to judge that the oxygen sensor 12 slightly degraded is degraded, the degradation judging line L3 close to the initial characteristic line Lin is determined. In contrast, when the driver desires to judge that the oxygen sensor 12 is not degraded even though the oxygen sensor 12 is slightly degraded, the degradation judging line L3 far from the initial characteristic line Lin is determined.

Accordingly, because the judgement whether or not the oxygen sensor 12 is degraded is performed by using the two-dimensional Io-In map, even though an absolute value of the converged current value In decreases as a degradation degree of the oxygen sensor 12 gradually increases, the degradation judgement can be performed with a high accuracy.

In the second embodiment, the judgement whether or not the oxygen sensor 12 is degraded is performed by using the two-dimensional Io-In map. However, because the limiting current value Ip influences the relationship between the peak current value Io and the converged current value In, it is applicable that a degradation judging line be set in a three-dimensional Io-In-Ip map obtained by adding the limiting current value Ip to the two-dimensional Io-In map to strictly diagnose the degradation of the oxygen sensor 12.

Also, the open control is adopted in the second embodiment to set the heating current supplied to the heater 19 at a constant value. However, it is applicable that the feedback control be adopted in the same manner as in the first embodiment to control the internal resistance Zdc of the solid electrolyte layer 31 at a constant value. In this case, though the internal resistance Zdc does not change even though a degradation degree of the oxygen sensor 12 becomes high, because the resistance Rb of the resistor Rb decreases, an absolute value of the peak current value Io increases. Accordingly, the diagnosis of the degradation of the oxygen sensor 12 can be performed by using the Io-In map shown in FIG. 16.

(Third Embodiment)

A third embodiment in which the degradation of the oxygen sensor 12 is diagnosed by using the relationship between the peak current value Io and the internal resistance Zdc of the solid electrolyte layer 31 is described. That is, because the internal resistance Zdc and the converged current value In satisfies the relationship $Zdc=Vn/In$, the diagnosis of the degradation of the oxygen sensor 12 can be performed by using a Zdc-Io map in place of the Io-In map. Also, the open control is adopted to set the heating current (or the control duty DC) to a constant value in the third embodiment by a function of an open control circuit (not shown).

Figure 17:
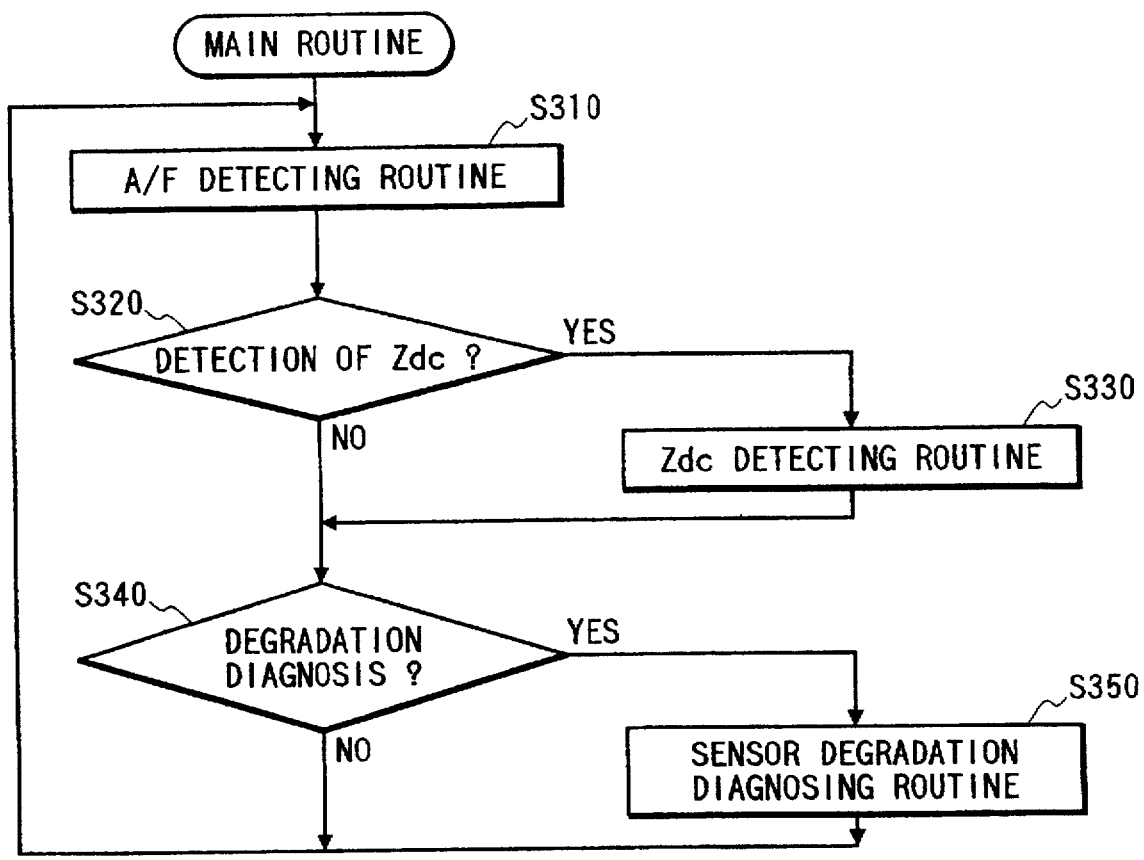
FIG. 17 is a flow chart of a main routine performed by the CPU according to a third embodiment.

FIG. 17 is a flow chart of a main routine performed by the CPU 22 according to a third embodiment.

As shown in FIG. 17, when the main routine is started, an air-fuel ratio detecting routine is performed by the CPU 22 in a step S310 in the same manner as in the step S110 shown in FIGS. 4 and 5. Thereafter, it is judged in a step S320 whether or not the internal resistance Zdc of the solid electrolyte layer 31 is to be detected. In this case, the judgement for the detection of the internal resistance Zdc is performed in the same manner as in the step S120 shown in FIG. 4. In cases where the detection of the internal resistance Zdc is required, an internal resistance detecting routine is performed in a step S330 in the same manner as in the step S130 shown in FIG. 6.

Thereafter, in cases where the detection of the internal resistance Zdc is not required in the step S320 or the internal resistance detecting routine is finished, it is judged in a step S340 whether or not the diagnosis of the degradation of the oxygen sensor 12 is performed. The judgement is performed in the same manner as in the step S160. In cases where the diagnosis of the degradation of the oxygen sensor is required, a sensor degradation diagnosing routine is performed in a step S350.

Figure 18:
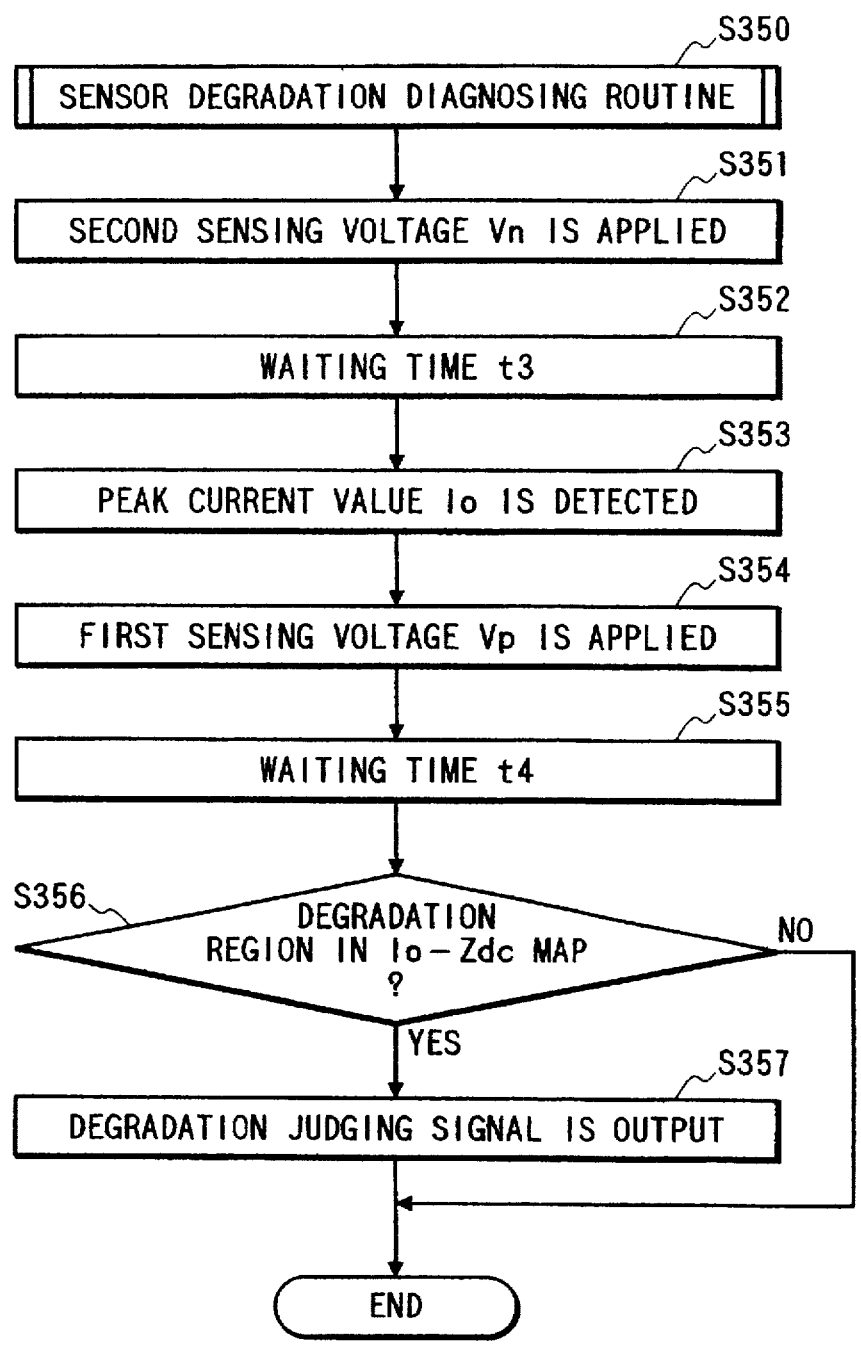
FIG. 18 is a flow chart of a sensor degradation diagnosing routine performed by the CPU according to the third embodiment.

FIG. 18 is a flow chart of the sensor degradation diagnosing routine performed by the CPU 22 according to the third embodiment.

As shown in FIG. 18, steps S351 to S355 are performed in the same manner as the steps S171 to S175. That is, the second sensing voltage Vn having a negative value is applied to the detecting device unit 18 in the step S351, the detection of the sensor current is waited by the third waiting time t3 in the step S352, a peak current value Io is detected in the step S353 and is stored in the RAM 24, the sensing voltage is changed to the first sensing voltage Vp having a positive value in the step S354, and the detection of the sensor current is waited by the fourth waiting time t4 in the step S355.

Figure 20:
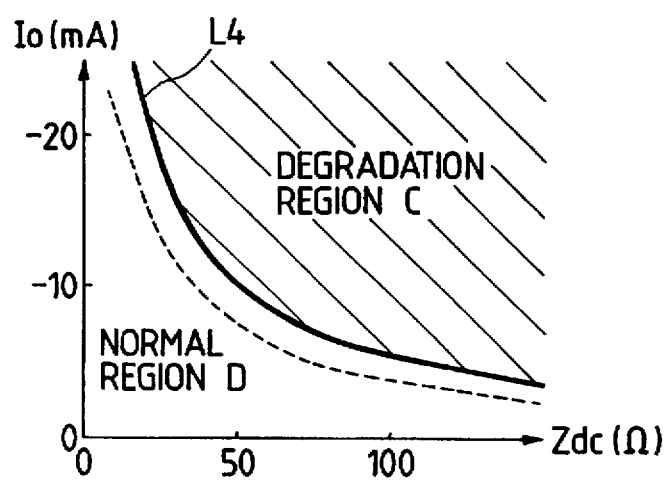
FIG. 20 shows an Io-Zdc map indicating a degradation region based on a relationship between a peak current value (Io) and an internal resistance (Zdc)

Thereafter, the judgement whether or not the oxygen sensor 12 is degraded is performed in a step S356 according to an Io-Zdc map which is stored in the ROM 23 in advance and indicates the relationship between the internal resistance Zdc and the peak current value Io. That is, as shown in FIG. 20, a whole region in the Io-Zdc map is divided by a degradation judging line L4 into a degradation region C and a normal region D, and a slope of the degradation judging line L4 becomes high as the degradation judging line L4 extends toward a lower value of the internal resistance Zdc.

In cases where an operation position (Zdc, Io) which is determined by the peak current value Io detected in the step S353 and the internal resistance Zdc detected in the step S330 is placed in the normal region D, it is judged by the CPU 22 that the oxygen sensor 12 normally functions, and the sensor degradation diagnosing routine is finished. In contrast, in cases where the operation position (Zdc, Io) is placed in the degradation region C, it is judged by the CPU 22 that the oxygen sensor 12 is degraded, and the procedure proceeds to a step S357.

In the step S357, a degradation judging signal is transmitted from the CPU 22 to the engine control unit 16, and the sensor degradation diagnosing routine is finished. In cases where the degradation judging signal is transmitted to the engine control unit 16, the alarm light 17 is operated to inform a user of the degradation of the oxygen sensor 12, and an air-fuel ratio feedback control performed by the engine control unit 16 to control the air-fuel ratio of the combustion gas to an optimum air-fuel ratio is stopped.

Figure 19:
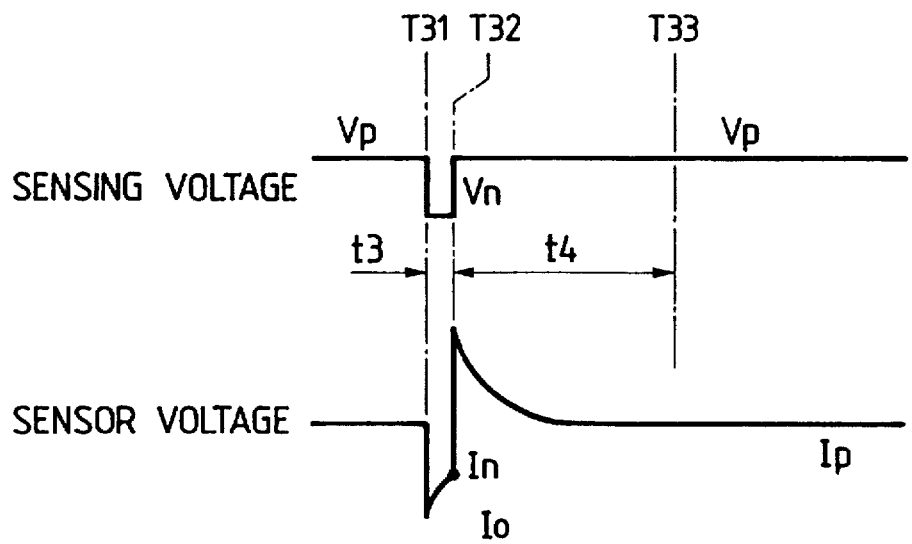
FIG. 19 is a time chart of a sensing voltage and a sensor current used in a sensor degradation diagnosing routine according to the third embodiment.

The sensor degradation diagnosing routine is concretely described by referring to a time chart shown in FIG. 19.

As shown in FIG. 19, the sensing voltage applied to the detecting device unit 18 is changed from the first sensing voltage Vp to the second sensing voltage Vn at a time T31. Thereafter, when the third waiting time t3 is elapsed, the peak current value Io is detected at a time T32, and the sensing voltage is returned to the first sensing voltage Vp at the same time T32. Thereafter, when the fourth waiting time t4 is elapsed, the limiting current value Ip is detected at a time T33, and the judgement whether or not the oxygen sensor 12 is degraded is performed by using the peak current value Io and the internal resistance Zdc.

The degradation judging line L4 of the Io-Zdc map shown in FIG. 20 is set as follows. That is, an initial characteristic of the oxygen sensor 12 is measured, and an initial relationship between an initial peak current value Ioi and an initial internal resistance Zdci corresponding to the initial characteristic is drawn in the Io-Zdc map. The initial relationship is indicated by an initial characteristic line Lin expressed by a dotted line in FIG. 20. Thereafter, the degradation judging line L4 is determined by shifting the initial characteristic line Lin toward a negative value direction of the peak current value Io by several % of the initial peak current value Ioi. A difference between the degradation judging line L4 and the initial characteristic line Lin depends on a degradation degree of the oxygen sensor 12 that a driver desires to judge as a degraded oxygen sensor. For example, when the driver desires to judge that the oxygen sensor 12 slightly degraded is degraded, the degradation judging line L4 close to the initial characteristic line Lin is determined. In contrast, when the driver desires to judge that the oxygen sensor 12 is not degraded even though the oxygen sensor 12 is slightly degraded, the degradation judging line L4 far from the initial characteristic line Lin is determined.

Accordingly, because the judgement whether or not the oxygen sensor 12 is degraded is performed according to the relationship between the internal resistance Zdc and the peak current value Io indicated by the two-dimensional Io-Zdc map, even though an absolute value of the internal resistance Zdc increases as a degradation degree of the oxygen sensor 12 gradually increases, the degradation judgement can be performed with a high accuracy in the same manner as in the first and second embodiments.

In the third embodiment, the judgement whether or not the oxygen sensor 12 is degraded is performed by using the two-dimensional Io-Zdc map. However, because the limiting current value Ip influences the relationship between the peak current value Io and the internal resistance Zdc, it is applicable that a degradation judging line be set in a three-dimensional Io-Zdc-Ip map obtained by adding the limiting current value Ip to the two-dimensional Io-Zdc map to strictly diagnose the degradation of the oxygen sensor 12.

Also, the open control is adopted in the third embodiment to set the heating current supplied to the heater 19 at a constant value. However, it is applicable that the feedback control such as a proportional integral (PI) control, a proportional integral and differential (PID) control or an integral (I) control be adopted for the heater 19 in the same manner as in the first embodiment to control the internal resistance Zdc of the solid electrolyte layer 31 at a constant value. In this case, though the internal resistance Zdc does not change even though a degradation degree of the oxygen sensor 12 becomes high, because the resistance Rb of the resistor Rb decreases, an absolute value of the peak current value Io increases. Accordingly, the diagnosis of the degradation of the oxygen sensor 12 can be performed by using the Io-Zdc map.

Also, it is applicable that a temperature of the detecting device unit 12 be controlled to a target temperature according to a detecting device temperature feedback control.

Also, in the first to third embodiments, the sensing voltage applied to the detecting device unit 18 is changed from the first sensing voltage Vp to the second sensing voltage Vn and is returned to the first sensing voltage vp to diagnose the degradation of the oxygen sensor 12 or detect the internal resistance Zdc. However, it is applicable that an alternating current impedance be used in the same manner as in a Published Japanese Patent Application No. 4-24657 of 1992 to diagnose the degradation of the oxygen sensor 12 or detect the internal resistance Zdc. In this case, an alternating voltage is applied to the oxygen sensor 12, and the diagnosis of the degradation of the oxygen sensor 12 or the detection of the internal resistance Zdc is performed according to an amplitude of the alternating voltage and an amplitude of the sensor current.

Also, it is applicable that the detection of the internal resistance Zdc be performed in the same manner as in a Published Japanese Patent Application No. 7-18837 of 1995.

Also, in the first to third embodiments, the peak current value Io is detected by changing the sensing voltage from the first sensing voltage Vp having a positive value to the second sensing voltage Vn having a negative value. However, it is applicable that a peak current value be detected by changing a voltage applied to the oxygen sensor 12 from a sensing voltage Vp having a negative value to another sensing voltage having a positive value. For example, because the sensing voltage is changed from the second sensing voltage Vn having a negative value to the first sensing voltage vp having a positive value at the time T2 shown in FIG. 10, the peak current value Io can be detected at a time just after the time T2.

Also, the peak current value Io can be detected even though the sensing voltage is changed from a first positive value (or a first negative value) to a second positive value (or a second negative value). In this case, following effects can be obtained. First, a configuration of a circuit for changing the sensing voltage can be simplified as compared with that in the change of the sensing voltage from a positive (or negative) value to a negative (or positive) value. In particular, in cases where the oxygen sensor 12 is used in the air-fuel lean ratio, the sensing voltage applied to the oxygen sensor 12 in an air-fuel ratio detecting operation is always positive. Therefore, the diagnosis of degradation of the oxygen sensor 12 performed by changing the sensing voltage from a positive (or negative) value to another positive (or negative) value can be easy. Secondly, because the sensing voltage applied to the oxygen sensor 12 is changed from the positive value Vp in the limiting current generating region to another positive value, a changing degree of the sensing voltage can be made small, and a changing degree of the sensor current can be also made small. Therefore, because a changing degree of the sensor current is small, the diagnosis of degradation of the oxygen sensor 12 can be performed with a higher accuracy. Thirdly, in cases where the oxygen sensor 12 is used in a very high air-fuel lean ratio, the sensing voltage applied to the oxygen sensor 12 in the air-fuel ratio detecting operation is a very high positive value. However, because a changing degree of the sensor current is small, the diagnosis of degradation of the oxygen sensor 12 can be easily performed even though the oxygen sensor 12 is used in a very high air-fuel lean ratio.

Figure 21:
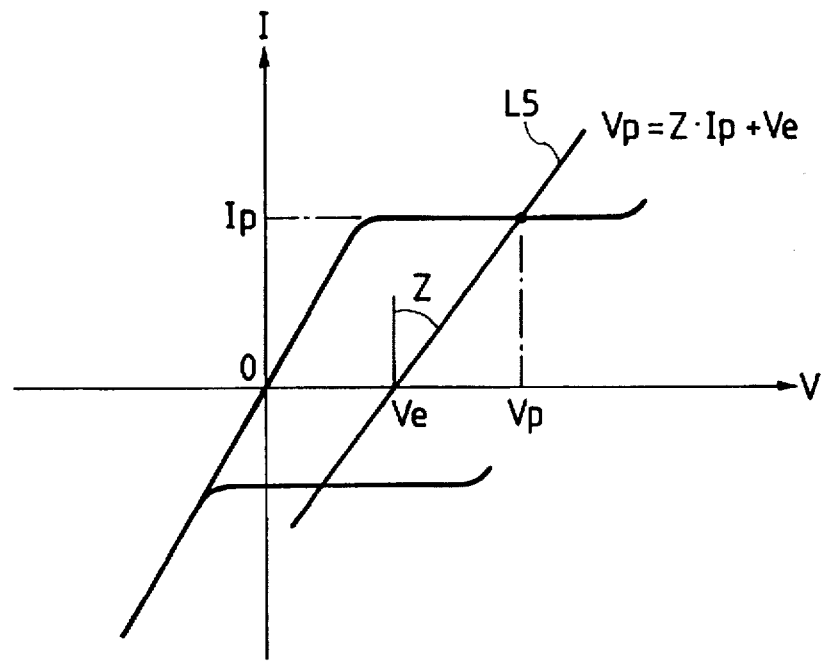
FIG. 21 shows a method for determining a first sensing voltage Vp changing with an actual air-fuel ratio by using voltage-current characteristic in the oxygen sensor.

Also, in the air-fuel ratio detecting routine of the first to third embodiments, the first sensing voltage Vp is determined on condition that a value Ip of the limiting current can be detected regardless of the increase and decrease of the air-fuel ratio changing in a desired detection range. However, it is applicable that the first sensing voltage Vp be changeably set. That is, as shown in FIG. 21, a sensing voltage setting line L5 satisfying the relationship V=Z*I+Ve is drawn in a V-I coordinate system, a limiting current value Ip corresponding to an actual air-fuel ratio detected by the microcomputer 20 is determined according to an air-fuel ratio feedback control, and the first sensing voltage Vp is determined on condition that a sensing voltage setting position (vp,Ip) is placed on the setting line L5 (Vp=Z*Ip+Ve). Here, a slop Z of the setting line L5 is almost the same as the internal resistance Zdc, and a position (Ve,0) is placed in the middle of a limiting current generating region corresponding to an ideal air-fuel ratio (Ip=0 mA). Therefore, the first sensing voltage Vp changes with the actual air-fuel ratio detected by the microcomputer 20. Accordingly, because the sensing voltage setting position (Vp,Ip) is always set in the middle of the limiting current generating region even though the actual air-fuel ratio detected by the microcomputer 20 changes, the limiting current value Ip can be reliably detected, and the degradation of the oxygen sensor 12 can be reliably diagnosed.

Also, in the first and third embodiments, the internal resistance Zdc is detected by detecting the converged current value In. However, it is applicable that a device temperature of the detecting device unit 18 be directly detected and the internal resistance Zdc be calculated according to a relationship between the device temperature and the internal resistance Zdc stored in the RAM 24.

(Fourth Embodiment)

Hereinafter, a method for diagnosing a malfunction (for example, a disconnection or a conducting defect) of an oxygen sensor used in an air-fuel ratio control apparatus of an automobile internal combustion engine is described according to a fourth embodiment with reference to drawings.

Figure 23:
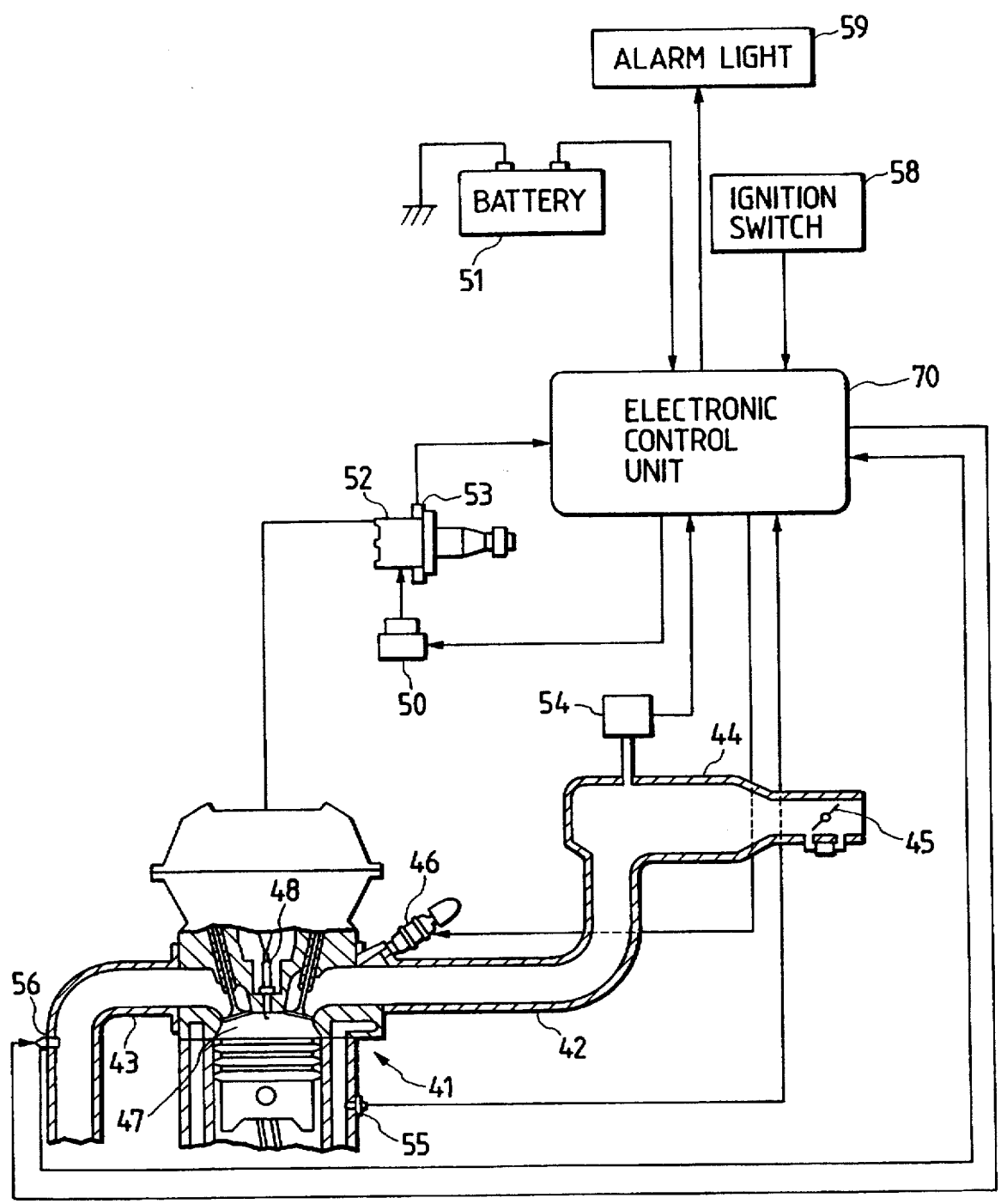
FIG. 23 is a constitutional view of an air-fuel ratio control apparatus of an automobile internal combustion engine according to a fourth embodiment.

FIG. 23 is a constitutional view of an air-fuel ratio control apparatus of an automobile internal combustion engine.

As shown in FIG. 23, an intake pipe 42 and an exhaust pipe 43 are respectively connected with a four-cylinder ignition type gasoline engine (hereinafter, merely called an engine) 41 for each cylinder of the engine 41. A surge tank 44 is arranged in the middle of the intake pipe 42, and a throttle valve 45 cooperating with an accel pedal (not shown) is arranged on an upper side of the surge tank 44. Also, an injector 46 is arranged in the intake pipe 42 of each cylinder of the engine 41 to inject and supply a fuel (or gasoline) into a combustion chamber 47 of each cylinder, and an ignition plug 48 is arranged in the combustion chamber 47 of each cylinder. A high voltage is produced in an igniter 50 from a voltage of a battery 51 and is distributed to each of the ignition plugs 48 by a distributer 52. A plurality of crank angle sensors 53 are arranged on the distributer 52 at prescribed crank angle intervals (for example, 30° crank angle intervals) to generate a crank angle signal in each of the crank angle sensors 53 while rotating a crank shaft of the engine 41. Also, a pressure sensor 54 is arranged on each surge tank 44 to detect a pressure (or an intake negative pressure) in the intake pipe 42. A water temperature sensor 55 is arranged on each cylinder block of the engine 41 to detect a temperature of an engine cooling water.

Also, a limiting current type oxygen sensor 56 is arranged in each exhaust pipe 43 of the engine 41, and a detecting signal of which a level linearly changes in proportion to an oxygen concentration of an exhaust gas is output from each oxygen sensor 56. A catalyst converter (not shown) is arranged on a lower stream side of each oxygen sensor 56, and the exhaust gas is purified by the catalyst converter. A detecting signal output from each sensor is input to an electronic control unit 70. The electronic control unit 70 is operated by using the battery 51 as an electric source, the operation of the engine 41 is started in synchronization with an "on" signal of an ignition switch 58, an air-fuel ratio correcting coefficient is corrected according to the detecting signal of each oxygen sensor 56 during the operation of the engine 41, and an actual air-fuel ratio is feedback-controlled to set the actual air-fuel rate to a target air-fuel rate (for example, a theoretical air-fuel rate). Also, a sensor malfunction diagnosing processing described later is performed by the electronic control unit 70, the existence of malfunction of the oxygen sensor 56 is diagnosed by the electronic control unit 70, an alarm light 59 is lighted on when it is judged that the malfunction of the oxygen sensor 56 exists, and the occurrence of the malfunction is informed a driver.

Figure 24:
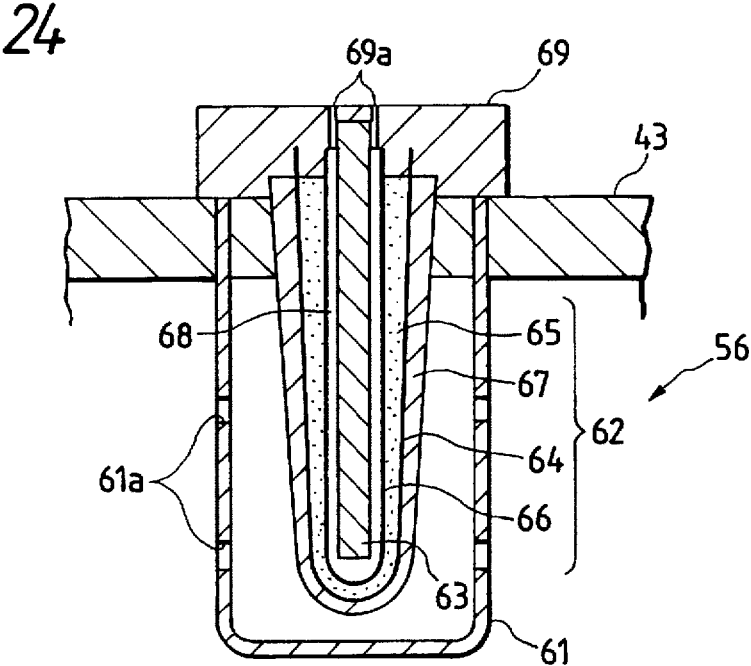
FIG. 24 is a cross sectional view of an oxygen sensor shown in FIG. 23.
Figure 25:
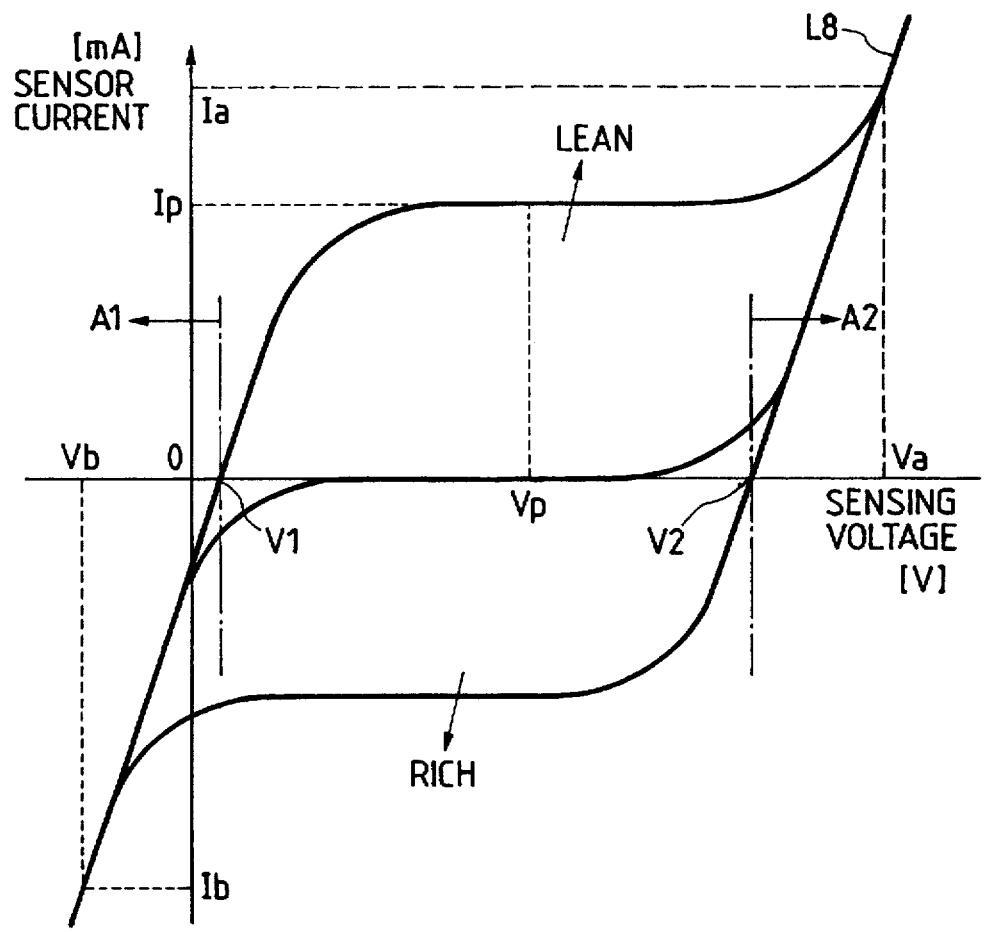
FIG. 25 shows a voltage-current characteristic of the oxygen sensor.

FIG. 24 is a cross sectional view of the oxygen sensor 56, and FIG. 25 shows a voltage-current characteristic of the oxygen sensor 56.

As shown in FIG. 24, the oxygen sensor 46 is projected into the exhaust pipe 43, and the oxygen sensor 46 is composed of a cover 61, a sensor body 62 and a heater 63. The cover 61 is formed in a U shape cross section, and many pores 61a are formed in the cover 61 to pass the exhaust gas from an outer surface to an inner surface. In the sensor body 62, a limiting current corresponding to an oxygen concentration of the exhaust gas in an air-fuel ratio lean region or corresponding to a combustible gas concentration of a carbon monoxide (CO) or the like in an air-fuel ratio rich region is generated.

The sensor body 62 is described in detail. In the sensor body 62, an exhaust gas side electrode layer 64 is attached on an outer surface of a solid electrolyte layer 65, and an atmosphere side electrode layer 66 is attached on an inner surface of the solid electrolyte layer 65. Also, a diffusion resistance layer 67 formed according to a plasma spraying technique is arranged on an outer surface of the exhaust gas side electrode layer 64. The solid electrolyte layer 65 is made of an oxygen ion conductive oxide sintered body in which CaO, MgO, $Y_2O_3$, $Yb_2O_3$ or the like is solution-treated in $ZrO_2$, $HfO_2$, $ThO_2$, $Bi_2O_3$ or the like as a stabilizer. The diffusion resistance layer 67 is made of a heat resistance inorganic body such as alumina, magnesia, silica, spinel, mullite or the like. The exhaust gas side electrode layer 64 and the atmosphere side electrode layer 66 are made of nobel metal having a high catalytic activity such as platinum and are placed on both surfaces of the solid electrolyte layer 65 as a porous chemical metal plating. The exhaust gas side electrode layer 64 has an area ranging from 10 to 100 $mm^2$ and a thickness ranging from 0.5 to 2.0 μm. The atmosphere side electrode layer 66 has an area of 10 $mm^2$ or more and a thickness ranging from 0.5 to 2.0 μm. The solid electrolyte layer 65 is equivalent to an oxygen concentration detecting device.

The heater 63 is placed in an atmosphere chamber 68 surrounded by the atmosphere side electrode layer 66 to heat the sensor body 62 composed of the atmosphere side electrode layer 66, the solid electrolyte layer 65, the exhaust gas side electrode layer 64 and the diffusion resistance layer 67. A heating capacity of the heater 63 is sufficient to activate the sensor body 62.

Also, a portion of the oxygen sensor 56 is exposed to outside the exhaust pipe 43, and a cap 69 is attached on the exposed portion of the oxygen sensor 5. An atmosphere leading hole 69a is formed in the cap 69 to lead the atmosphere into the atmosphere chamber 68.

In the above configuration of the oxygen sensor 56, a concentration electromotive force is generated at a theoretical air-fuel ratio point by the sensor body 62, and a limiting current of which a value corresponds to an oxygen concentration (or a flow of oxygen ions in the solid electrolyte layer 65) of the exhaust gas is generated by the sensor body 62 in cases where an air-fuel ratio in a combustion gas shifts from the theoretical air-fuel ratio point to the air-fuel ratio lean region. In this case, a value of the limiting current corresponding to the oxygen concentration is determined by the area of the exhaust gas side electrode layer 64, the thickness of the diffusion resistance layer 67, a porous ratio and an average porous diameter in the exhaust gas side electrode layer 64 and a porous ratio and an average porous diameter in the atmosphere side electrode layer 66. Also, though the oxygen concentration can be detected according to a linear characteristic, it is required to heat the sensor body 62 at a temperature of 650° C. or more for the purpose of activating the sensor body 62, and an activating region for the sensor body 62 cannot be controlled by heating the sensor body 62 only with the exhausted gas of the engine 41 because an activating temperature range of the sensor body 62 is narrow. Therefore, a temperature of the sensor body 62 is controlled according to a heating control using the heater 63. Also, in cases where an air-fuel ratio in a combustion gas shifts from the theoretical air-fuel ratio point to the air-fuel ratio rich region, an unburned gas remains in the exhaust gas as a carbon monoxide (CO), a CO concentration of the exhaust gas linearly changes with an air-fuel ratio in the combustion gas, and a limiting current of which a value corresponds to the CO concentration of the exhaust gas is generated by the sensor body 62.

Also, as shown in FIG. 25, the voltage-current characteristic of the oxygen sensor 56 indicates that a relationship between a sensor current which passes through the solid electrolyte layer 65 of the sensor body 56 and is proportional to an oxygen concentration (or an air-fuel ratio) detected by the oxygen sensor 56 and a sensing voltage applied to the solid electrolyte layer 65 is linear. When the sensor body 56 is set to an active condition, the voltage-current characteristic of the oxygen sensor 56 is indicated by a characteristic line L8, and the sensor body 56 is set to the most stable condition. In this case, a straight line segment of the characteristic line L8 parallel to a voltage axis specifies a limiting current output from the sensor body 56. The increase and decrease of the limiting current depends on the air-fuel ratio (or lean or rich). That is, as the air-fuel ratio shifts to the rich side, the value of the limiting current increases. In contrast, as the air-fuel ratio shifts to the lean side, the value of the limiting current decreases.

Also, a region for a line segment of the characteristic line L8 placed at a lower sensing voltage than the straight line segment of the characteristic line L8 parallel to the voltage axis is called a resistance governing region, and a slope of the characteristic line L8 in the resistance governing region is specified by an internal resistance of the solid electrolyte layer 65. Because the internal resistance of the solid electrolyte layer 65 changes with the temperature of the sensor body 62. That is, when the temperature of the sensor body 62 decreases, the internal resistance of the solid electrolyte layer 65 increases, and the slope of the characteristic line L8 in the resistance governing region becomes low. Also, the value of the limiting current corresponding to the theoretic air-fuel rate is zero. Also, the characteristic line L8 in the resistance governing region slightly shifts toward a positive sensing voltage side because of the concentration electromotive force of the oxygen sensor 56. That is, the characteristic line L8 in the resistance governing region crosses the sensing voltage axis at a positive value V1.

When a sensing voltage Vp is applied to the solid electrolyte layer 65 of the sensor body 62, a characteristic line L8 corresponding to an actual air-fuel ratio is determined, and a value Ip of the limiting current indicated by the characteristic line L8 is detected. In cases where the engine 41 is a lean-burn engine in which a combustion gas of the air-fuel ratio lean region is burned, the value of the limiting current is always positive. Also, in the lean-burn engine, when a sensing voltage having a negative value Vb is applied to the solid electrolyte layer 65 of the sensor body 62, a negative value Ib of a sensor current which flows the sensor body 62 without depending on the oxygen concentration is detected. The negative value Ib of the sensor current is proportional to the temperature of the sensor body 62. Also, in cases where a combustion gas of the air-fuel ratio rich region is burned, when a sensing voltage having a positive value v in the limiting current generating region is applied to the solid electrolyte layer 65 of the sensor body 62, a limiting current corresponding to a rich air-fuel ratio is detected, and the value of the limiting current is negative.

Also, as shown in FIG. 25, the voltage V1 is lower than a lowest voltage in the limiting current generating region (or a flatness region agreeing with the voltage axis) corresponding to the ideal air-fuel ratio (almost equal to 14.7), and a voltage region (shown in FIG. 25 by a symbol A1) lower than the voltage V1 is equivalent to a region in which a sensor current always has a negative value for any air-fuel ratio. Also, a voltage V2 is higher than a highest voltage in the limiting current generating region corresponding to the ideal air-fuel ratio, and a voltage region (shown in FIG. 25 by a symbol A2) higher than the voltage V2 is equivalent to a region in which a sensor current always has a positive value for any air-fuel ratio.

Figure 26:
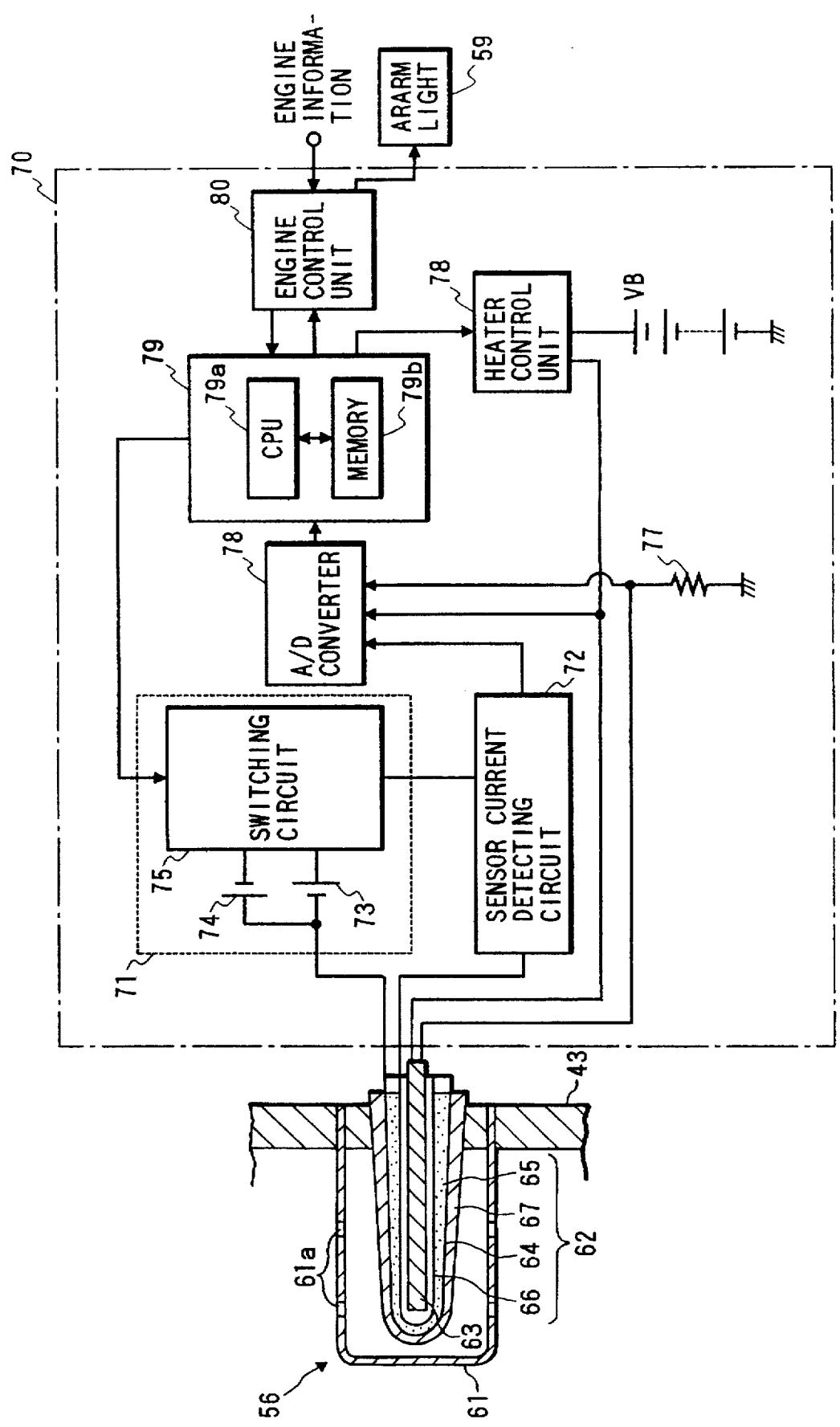
FIG. 26 is a block diagram of an electronic control unit shown in FIG. 23.

FIG. 26 is a block diagram of the electronic control unit 70. As shown in FIG. 26, a bias control unit 71 is connected to the exhaust gas side electrode layer 64 of the sensor body 62, and the atmosphere side electrode layer 66 of the sensor body 62 is connected to the bias control unit 71 through a sensor current detecting circuit 72. The bias control unit 71 comprises a first direct current source 73 for a positive bias, a second direct current source 74 for a negative bias, and a switching circuit 75. A negative side electrode of the first direct current source 73 and a positive side electrode of the second direct current source 74 are respectively connected to the exhaust gas side electrode layer 64.

When the switching circuit 75 is set to a first change-over condition, a positive side electrode of the first direct current source 73 is only connected to the switching circuit 75. In contrast, when the switching circuit 75 is set to a second change-over condition, a negative side electrode of the second direct current source 74 is only connected to the switching circuit 75. That is, when the switching circuit 75 is set in the first change-over condition, the solid electrolyte layer 65 of the sensor body 62 is biased toward a positive voltage by the first direct current source 73, and a first current directed in a positive direction flows through the solid electrolyte layer 65. In contrast, when the switching circuit 75 is set in the second change-over condition, the solid electrolyte layer 65 of the sensor body 62 is biased toward a negative voltage by the second direct current source 74, and a second current directed in a negative direction flows through the solid electrolyte layer 65.

A sensor current passing from the atmosphere side electrode layer 66 of the sensor body 62 to the switching circuit 75 and another sensor current passing from the switching circuit 75 to the atmosphere side electrode layer 66 flow through the solid electrolyte layer 65, and these sensor currents are detected by the sensor current detecting circuit 72. Also, an electric power supplied from a battery VB to the heater 63 is duty-controlled by a heater control circuit 76 according to a temperature of the sensor body 62 and a temperature of the heater 63 to control the heating of the heater 63. A heater current supplied to the heater 63 is detected by a current detecting resistor 77. Each sensor current, the heater current supplied to the heater 63 and a sensing voltage applied to the exhaust gas side electrode layer 64 are respectively converted into a digital signal by an analog-digital converter 78, and the digital signal is transmitted to a microcomputer 79. The microcomputer 79 comprises a central processing unit (CPU) 79a for performing various arithmetic processings and a memory 79b composed of a read only memory (ROM) and a random access memory (RAM). The bias control circuit 71 and the heater control circuit 76 are controlled by the microcomputer 79 according to a computer program stored in the memory 79b. Various sensor signals are input to an engine control unit 80 as pieces of engine information, and the pieces of engine information such as an intake air temperature, an intake air negative pressure, a cooling water temperature, an engine speed and an automobile speed are detected by the engine control unit 80. Thereafter, a fuel injection performed by each injector 46 is controlled according to the engine information by the engine control unit 80. Also, the alarm light 59 is lighted on by the engine control unit 80 according to a malfunction judging signal transmitted from the microcomputer 79. In this embodiment, the CPU 79a of the microcomputer functions as a voltage applying means and a malfunction diagnosing means.

In the above configuration, an air-fuel ratio detecting operation and a malfunction diagnosing operation are described.

Figure 27:
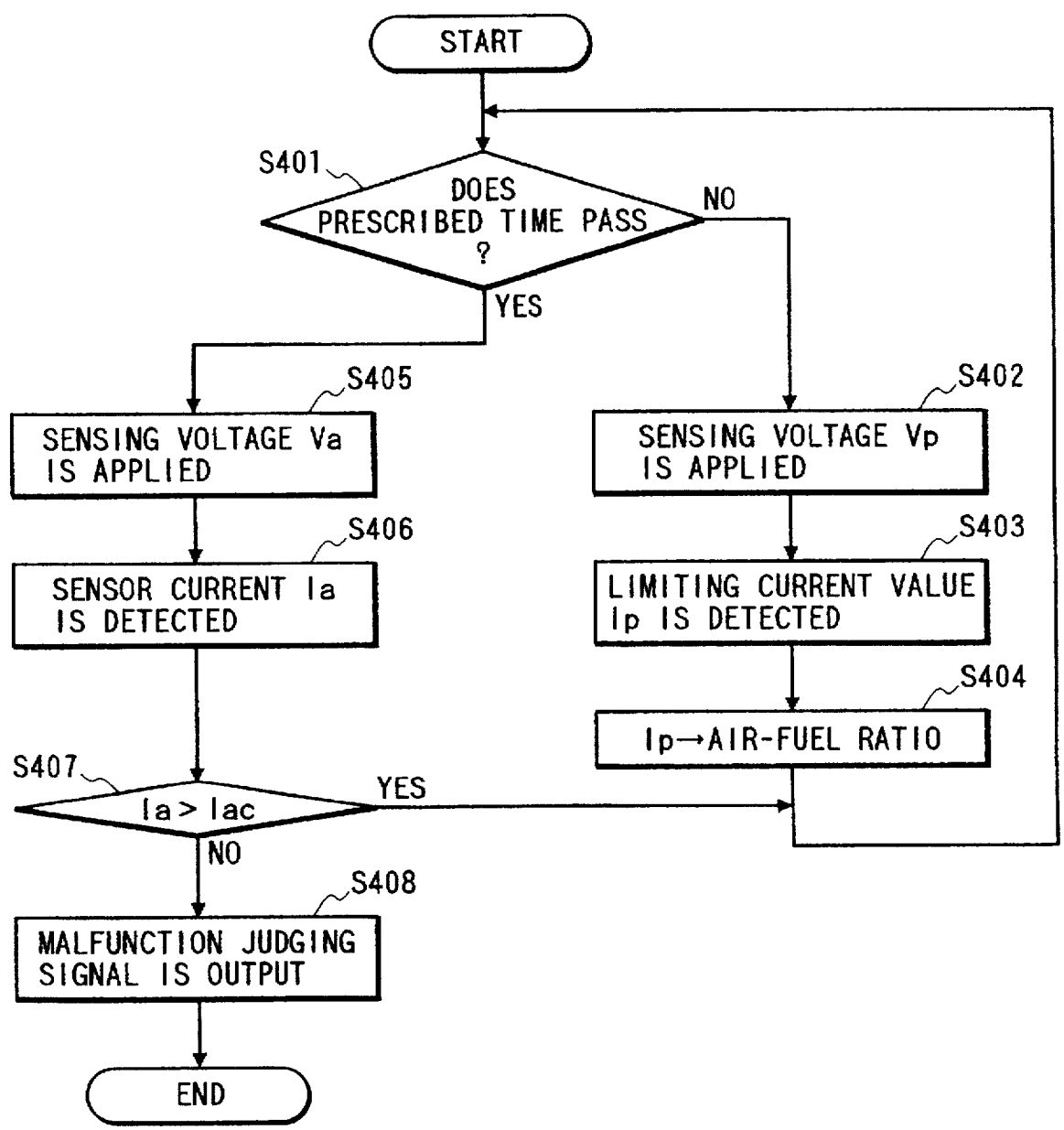
FIG. 27 is a flow chart showing an air-fuel ratio detecting routine in which an air-fuel ratio detection and a malfunction diagnosis for the oxygen sensor are performed according to the fourth embodiment.

FIG. 27 is a flow chart showing an air-fuel ratio detecting routine performed by the CPU 79a of the microcomputer 79 to perform an air-fuel ratio detection and the diagnosis of malfunction of the oxygen sensor 56.

As shown in FIG. 27, when the ignition switch 58 is turned on, an electric power is supplied from the battery 51 to the electronic control unit 70, and an air-fuel ratio detecting routine is started. In a step S401, it is judged by the CPU 79a whether or not a prescribed time (for example, one to several seconds) passes after a previous malfunction diagnosis. In cases where the prescribed time does not pass, an air-fuel ratio detecting operation is performed in steps S402 to S404. In contrast, in cases where the prescribed time passes, a malfunction diagnosing operation is performed in steps S405 to S410.

In detail, in case of the air-fuel ratio detecting operation, a sensing voltage Vp is set by the CPU 79a in a step S402 to detect an air-fuel ratio, and the sensing voltage Vp is applied to the oxygen sensor 56. In this case, a fixed value is available for the sensing voltage Vp, and a changeable value is available for the sensing voltage Vp. In cases where the sensing voltage Vp having a changeable value is applied to the oxygen sensor 56, as shown in FIG. 21, the sensing voltage Vp corresponding to a limiting current value Ip (or an air-fuel ratio) recently detected is set according to an equation Vp=Z*Ip+Ve. After the sensing voltage Vp is applied, a limiting current value Ip detected by the sensor current detecting circuit 72 is transmitted to the CPU 79a in a step S403, and an air-fuel ratio corresponding to the limiting current value Ip is calculated according to the relationship between the limiting current and the air-fuel ratio shown in FIG. 9 in a step S404. The calculated air-fuel ratio is transmitted from the CPU 79a to the engine control unit 80, and an air-fuel ratio feedback control is performed by the engine control unit 80 according to the calculated air-fuel ratio. The air-fuel ratio detecting operation in the steps S402 to S404 is repeated until it is judged in the step S401 that the prescribed time passes.

Thereafter, the malfunction diagnosing operation is performed at prescribed intervals. In detail, a sensing voltage having a positive value Va (Va>V2) placed in the A2 region is applied to the exhaust gas side electrode layer 64 of the sensor body 62 in a step S405 as a diagnosing voltage. In this case, a sensor current Ia determined by the sensing voltage Va according to the voltage-current characteristics is always positive for any air-fuel ratio, and Va=1.0 V is set.

Figure 22A:
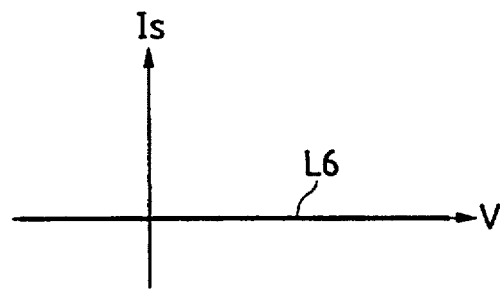
FIGS. 22A and 22B respectively show a malfunction condition of an oxygen sensor.
Figure 22B:
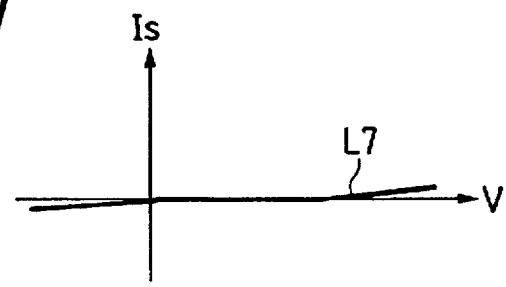

After the sensing voltage Va is applied, a sensor current having a positive value Ia is detected by the sensor current detecting circuit 72 in a step S406, and it is judged in a step S407 whether or not the value Ia of the sensor current is higher than a prescribed malfunction judging value Iac (for example, Iac=1 mA). In cases where the oxygen sensor 56 normally functions, because the value Ia of the sensor current is higher than the prescribed malfunction judging value Iac, the procedure returns to the step S401. In contrast, in cases where a malfunction of the oxygen sensor 56 occurs, because the value Ia of the sensor current becomes almost equal to zero as shown in FIGS. 22A and 22B, a malfunction judging signal is output to the engine control unit 80 in a step S408. Therefore, the alarm light 59 is lighted on under control of the engine control unit 80 according to the malfunction judging signal, and the air-fuel ratio control performed by the engine control unit 80 is stopped.

Accordingly, because the malfunction diagnosing operation is performed by applying the sensing voltage having the positive value Va to the exhaust gas side electrode layer 64 as a malfunction diagnosing voltage, the malfunction diagnosis of the oxygen sensor 56 can be easily performed with a high accuracy.

Also, because the sensing voltage applied to the sensor body 62 is changed from the positive value Vp in the limiting current generating region to the positive value Va, a configuration of the switching circuit 75 can be simplified as compared with that in the change of the sensing voltage from a positive (or negative) value to a negative (or positive) value. In particular, in cases where the oxygen sensor 56 is used in the air-fuel lean ratio, the sensing voltage applied to the sensor body 62 in the air-fuel ratio detecting operation is always positive. Therefore, the diagnosis of a malfunction of the oxygen sensor 56 performed by changing the sensing voltage from a positive value to another positive value can be easy.

Also, because the sensing voltage applied to the sensor body 62 is changed from the positive value Vp in the limiting current generating region to the positive value Va, a changing degree of the sensing voltage can be made small, and a changing degree of the sensor current can be also made small. Therefore, because a changing degree of the sensor current is small, the diagnosis of a malfunction of the oxygen sensor 56 can be performed with a higher accuracy.

Also, in cases where the oxygen sensor 56 is used in a very high air-fuel lean ratio, the sensing voltage applied to the sensor body 62 in the air-fuel ratio detecting operation is a very high positive value. However, because a changing degree of the sensor current is small, the diagnosis of a malfunction of the oxygen sensor 56 can be easily performed even though the oxygen sensor 56 is used in a very high air-fuel lean ratio.

In the fourth embodiment, the positive value Va=1.0 V is set. However, the positive value Va of the sensing voltage is not limited on condition that the sensing voltage is placed in the A2 region.

Also, the sensing voltage applied to the exhaust gas side electrode layer 64 as a malfunction diagnosing voltage is not limited to a positive value. That is, it is applicable that the malfunction diagnosing operation be performed by applying a sensing voltage having the negative value Vb (Vb<V1) to the exhaust gas side electrode layer 64 as a malfunction diagnosing voltage. In detail, because the slope of the characteristic line L8 in the resistance governing region is equivalent to the internal resistance value of the sensor body 62, a value V1 at the intersection of the characteristic line L8 and the voltage axis is calculated from the internal resistance value of the sensor body 62, and the negative value Vb of the sensing voltage is set. In this case, because the sensor current Ib determined by the sensing voltage Vb according to the voltage-current characteristics is always negative for any air-fuel ratio in cases where the oxygen sensor 56 normally functions, the malfunction diagnosis of the oxygen sensor 56 can be easily performed with a high accuracy.

Also, in the fourth embodiment, the sensing voltage applied to the sensor body 62 is changed from the positive value Vp in the limiting current generating region to the positive value Va, the sensor current output from the oxygen sensor 56 is detected, and a malfunction of the oxygen sensor 56 is diagnosed. However, in cases where a temperature of the oxygen sensor 56 is, for example, very low and the limiting current corresponding to a negative sensing voltage is detected, it is applicable that the sensing voltage applied to the sensor body 62 be changed from a negative value in the limiting current generating region to another negative value in the resistance governing region and a malfunction of the oxygen sensor 56 be diagnosed.

Having illustrated and described the principles of the present invention in a preferred embodiment thereof, it should be readily apparent to those skilled in the art that the invention can be modified in arrangement and detail without departing from such principles. We claim all modifications coming within the spirit and scope of the accompanying claims.

What is claimed is:

1. A method for diagnosing degradation of an oxygen sensor from which a limiting current corresponding to an oxygen concentration is output according to a voltage-current characteristic by applying a sensing voltage placed in a limiting current generating region, comprising the steps of:

changing the sensing voltage applied to the oxygen sensor from a first sensing voltage to a second sensing voltage which is placed outside the limiting current generating region to output a sensing current having a current peak from the oxygen sensor;

detecting a peak current value of the sensing current output from the oxygen sensor;

judging whether or not the peak current value of the sensing current is within a normal range; and diagnosing the oxygen sensor to be degraded in cases where it is judged that the peak current value of the sensing current is not within the normal range.

2. A method for diagnosing degradation of an oxygen sensor according to claim 1 in which the first sensing voltage is a positive value, and a second sensing voltage is a negative value.

3. A method for diagnosing degradation of an oxygen sensor according to claim 1 in which the first sensing voltage and the second sensing voltage are a positive value or a negative value together.

4. A method for diagnosing degradation of an oxygen sensor according to claim 1 in which the step of judging whether or not the peak current value of the sensing current is within a normal range comprises the steps of:

waiting by a prescribed time until the sensing current output from the oxygen sensor is converged to a converged current value;

detecting the converged current value of the sensing current;

changeably determining the normal range depending on the converged current value; and judging whether or not the peak current value of the sensing current is within the normal range depending on the converged current value.

5. A method for diagnosing degradation of an oxygen sensor according to claim 1 in which the step of judging whether or not the peak current value of the sensing current is within a normal range comprises the steps of:

waiting by a prescribed time until the sensing current output from the oxygen sensor is converged to a converged current value;

detecting the converged current value of the sensing current;

determining a degradation region and a normal region divided by a degradation judging line which is extended in an area defined by the peak current value and the converged current value on condition that a change of an absolute value of the peak current value is larger than another change of an absolute value of the converged current value;

regarding the normal region as the normal range; and judging whether or not the peak current value of the sensing current is within the normal range depending on the converged current value.

6. A method for diagnosing degradation of an oxygen sensor according to claim 1 in which the step of judging whether or not the peak current value of the sensing current is within a normal range comprises the steps of:

detecting an internal resistance of the oxygen sensor;

determining the normal range depending on the internal resistance of the oxygen sensor; and judging whether or not the peak current value of the sensing current is within the normal range depending on the internal resistance.

7. A method for diagnosing degradation of an oxygen sensor according to claim 6 in which the step of detecting an internal resistance, comprising the steps of:

waiting by a prescribed time until the sensing current output from the oxygen sensor is converged to a converged current value;

detecting the converged current value of the sensing current; and calculating the internal resistance of the oxygen sensor from the converged current value and the second sensing voltage.

8. A method for diagnosing degradation of an oxygen sensor according to claim 1 in which the step of judging whether or not the peak current value of the sensing current is within a normal range comprises the steps of:

detecting an internal resistance of the oxygen sensor;

determining a degradation region and a normal region divided by a degradation judging line which is extended in an area defined by the peak current value and the internal resistance on condition that a change of an absolute value of the peak current value becomes smaller as the internal resistance becomes higher;

regarding the normal region as the normal range; and judging whether or not the peak current value of the sensing current is within the normal range depending on the internal resistance.

9. A method for diagnosing degradation of an oxygen sensor according to claim 8 in which the step of detecting an internal resistance, comprising the steps of:

waiting by a prescribed time until the sensing current output from the oxygen sensor is converged to a converged current value;

detecting the converged current value of the sensing current; and calculating the internal resistance of the oxygen sensor from the converged current value and the second sensing voltage.

10. A method for diagnosing degradation of an oxygen sensor according to claim 1 in which the step of detecting a peak current value of the sensing current output from the oxygen sensor comprises the steps of:

waiting by a prescribed short time;

detecting the peak current value of the sensing current output from the oxygen sensor before the peak current value of the sensing current is converged.

11. A method for diagnosing degradation of an oxygen sensor according to claim 1 in which the step of changing the sensing voltage further comprise the step of:

setting the first sensing voltage to a value placed in the middle of the limiting current generating region;

applying the first sensing voltage to the oxygen sensor to obtain a current limiting current;

calculating a current air-fuel ratio in a combustion gas from the current limiting current; and controlling an air-fuel ratio in the combustion gas to an optimum air-fuel ratio.

12. A method for diagnosing malfunction of an oxygen sensor from which a limiting current corresponding to an oxygen concentration is output according to a voltage-current characteristic by applying a sensing voltage placed in a limiting current generating region, comprising the steps of:

setting a particular sensing voltage at a positive or negative value outside the limiting current generating region;

applying the particular sensing voltage to the oxygen sensor;

detecting a particular sensing current output from the oxygen sensor;

judging whether or not a value of the particular sensing current is within a desired current value range; and informing of a malfunction of the oxygen sensor in cases where the value of the particular sensing current is not within the desired current value range.

13. A method for diagnosing malfunction of an oxygen sensor according to claim 12 in which the step of judging whether or not a value of the particular sensing current is within a desired current value range, comprising the steps of:

judging whether or not the value of the particular sensing current is zero;

judging that the oxygen sensor normally functions in cases where the value of the particular sensing current is positive or negative; and judging that a malfunction exists in the oxygen sensor in cases where the value of the particular sensing current is zero.

14. A method for diagnosing malfunction of an oxygen sensor according to claim 12 in which the step of setting a particular sensing voltage comprising the steps of:

setting the particular sensing voltage at a first positive value of the limiting current generating region to detect a particular limiting current; and changing the particular sensing voltage from the first positive value to a second positive value outside the limiting current generating region.

15. A method for diagnosing malfunction of an oxygen sensor according to claim 12 in which the step of setting a particular sensing voltage comprising the steps of:

setting the particular sensing voltage at a first negative value of the limiting current generating region to detect a particular limiting current; and changing the particular sensing voltage from the first negative value to a second negative value outside the limiting current generating region.

16. An apparatus for diagnosing degradation of an oxygen sensor from which a limiting current corresponding to an oxygen concentration is output according to a voltage-current characteristic by applying a sensing voltage placed in a limiting current generating region, comprising:

voltage changing means for changing the sensing voltage applied to the oxygen sensor from a first sensing voltage to a second sensing voltage which is placed outside the limiting current generating region;

current change detecting means for detecting a change of the sensor current output from the oxygen sensor to which the second sensing voltage is applied by the voltage changing means and detecting a peak current value of the sensing current;

degradation diagnosing means for diagnosing degradation of the oxygen sensor according to the peak current value detected by the current change detecting means by judging whether or not the peak current value of the sensing current is within a normal range;

degradation judging means for judging that the oxygen sensor is degraded in cases where it is judged by the degradation diagnosing means that the peak current value of the sensing current is not within the normal range and outputting a degradation judging signal; and alarming means for displaying the degradation of the oxygen sensor according to the degradation judging signal output from the degradation judging means.

* * * * *